(12) United States Patent
Whitehurst et al.

(10) Patent No.: US 7,493,171 B1
(45) Date of Patent: Feb. 17, 2009

(54) TREATMENT OF PATHOLOGIC CRAVING AND AVERSION SYNDROMES AND EATING DISORDERS BY ELECTRICAL BRAIN STIMULATION AND/OR DRUG INFUSION

(75) Inventors: Todd K Whitehurst, Santa Clarita, CA (US); James C Makous, Santa Clarita, CA (US); Rafael Carbunaru, Studio City, CA (US); Kristen N Jaax, Saugus, CA (US)

(73) Assignee: Boston Scientific Neuromodulation Corp., Valencia, CA (US)

( * ) Notice: Subject to any disclaimer, the term of this patent is extended or adjusted under 35 U.S.C. 154(b) by 243 days.

(21) Appl. No.: 11/140,152

(22) Filed: May 27, 2005

Related U.S. Application Data

(63) Continuation-in-part of application No. 09/993,086, filed on Nov. 6, 2001, now Pat. No. 6,950,707.

(60) Provisional application No. 60/252,625, filed on Nov. 21, 2000.

(51) Int. Cl.
*A61N 1/00* (2006.01)

(52) U.S. Cl. .............................. 607/58; 607/45; 128/898

(58) Field of Classification Search .................. 607/45, 607/58
See application file for complete search history.

(56) References Cited

U.S. PATENT DOCUMENTS

| | | | |
|---|---|---|---|
| 4,646,744 A | 3/1987 | Capel | |
| 5,188,104 A | 2/1993 | Wernicke et al. | |
| 5,193,539 A | 3/1993 | Schulman et al. | |
| 5,193,540 A | 3/1993 | Schulman et al. | |
| 5,231,988 A | 8/1993 | Wernicke et al. | |
| 5,263,480 A | 11/1993 | Wernicke et al. | |
| 5,312,439 A | 5/1994 | Loeb | |
| 5,324,316 A | 6/1994 | Schulman et al. | |
| 5,405,367 A | 4/1995 | Schulman et al. | |
| 5,487,739 A | 1/1996 | Aebischer et al. | |
| 5,496,369 A | 3/1996 | Howard, III | |
| 5,540,734 A | 7/1996 | Zabara | |

(Continued)

FOREIGN PATENT DOCUMENTS

| | | |
|---|---|---|
| WO | WO-92/13592 | 8/1992 |

(Continued)

OTHER PUBLICATIONS

Ahren, et al., "The Mechanism of Vagal Nerve Stimulation of Glucagon and Insulin Secretion in the Dog", Endocrinology, vol. 118, No. 4, (Apr. 1986) pp. 1551-1557.

(Continued)

*Primary Examiner*—George Manuel
*Assistant Examiner*—Christopher A Flory
(74) *Attorney, Agent, or Firm*—AdvantEdge Law Group, LLC

(57) ABSTRACT

Systems and methods for introducing one or more stimulating drugs and/or applying electrical stimulation to the brain to at least treat or prevent obesity and/or other eating disorders, as well as drug, nicotine and alcohol addiction, uses at least one system control unit (SCU) producing electrical pulses delivered via electrodes implanted in the brain and/or producing drug infusion pulses, wherein the stimulating drug(s) are delivered to targeted areas in the brain.

15 Claims, 13 Drawing Sheets

U.S. PATENT DOCUMENTS

| | | | |
|---|---|---|---|
| 5,589,183 A | 12/1996 | Jannetta | |
| 5,597,797 A | 1/1997 | Clark | |
| 5,697,975 A | 12/1997 | Howard, III et al. | |
| 5,741,211 A | 4/1998 | Renirie et al. | |
| 5,782,798 A * | 7/1998 | Rise | 604/500 |
| 5,792,210 A * | 8/1998 | Wamubu et al. | 607/58 |
| 5,833,600 A * | 11/1998 | Young | 600/300 |
| 5,843,093 A | 12/1998 | Howard, III | |
| 5,919,216 A | 7/1999 | Houben et al. | |
| 5,989,920 A | 11/1999 | Gerald | |
| 6,006,124 A | 12/1999 | Fischell et al. | |
| 6,016,449 A | 1/2000 | Fischell et al. | |
| 6,051,017 A | 4/2000 | Loeb et al. | |
| 6,093,167 A | 7/2000 | Houben et al. | |
| 6,094,598 A | 7/2000 | Elsberry et al. | |
| 6,129,685 A | 10/2000 | Howard, III | |
| 6,167,311 A * | 12/2000 | Rezai | 607/45 |
| 6,171,239 B1 | 1/2001 | Humphrey | |
| 6,269,270 B1 | 7/2001 | Boveja | |
| 6,284,729 B1 | 9/2001 | Bernfield et al. | |
| 6,353,762 B1 | 3/2002 | Baudino et al. | |
| 6,374,140 B1 | 4/2002 | Rise | |
| 6,415,184 B1 | 7/2002 | Ishikawa et al. | |
| 6,609,030 B1 * | 8/2003 | Rezai et al. | 607/45 |
| 6,782,292 B2 | 8/2004 | Whitehurst | |
| 6,907,280 B2 * | 6/2005 | Becerra et al. | 600/407 |
| 6,926,660 B2 * | 8/2005 | Miller | 600/9 |
| 7,077,822 B1 * | 7/2006 | Howard, III | 604/93.01 |
| 2002/0013612 A1 * | 1/2002 | Whitehurst | 607/45 |
| 2002/0032177 A1 * | 3/2002 | Allan et al. | 514/129 |
| 2002/0058867 A1 * | 5/2002 | Breiter et al. | 600/407 |
| 2002/0151939 A1 * | 10/2002 | Rezai | 607/40 |
| 2003/0096785 A1 * | 5/2003 | Stricker-Krongrad et al. | 514/44 |
| 2003/0166648 A1 * | 9/2003 | MacDonald | 514/228.2 |
| 2004/0136971 A1 * | 7/2004 | Scharp et al. | 424/93.7 |
| 2004/0138111 A1 * | 7/2004 | Draghia-Akli et al. | 514/12 |
| 2004/0193001 A1 * | 9/2004 | Miller | 600/9 |
| 2004/0193229 A1 * | 9/2004 | Starkebaum et al. | 607/40 |
| 2005/0048641 A1 * | 3/2005 | Hildebrand et al. | 435/283.1 |
| 2005/0049650 A1 | 3/2005 | Nuttin et al. | |
| 2005/0065574 A1 * | 3/2005 | Rezai | 607/45 |
| 2005/0075701 A1 * | 4/2005 | Shafer | 607/72 |
| 2005/0143787 A1 * | 6/2005 | Boveja et al. | 607/45 |
| 2005/0192644 A1 * | 9/2005 | Boveja et al. | 607/45 |
| 2005/0209654 A1 * | 9/2005 | Boveja et al. | 607/45 |
| 2006/0074298 A1 * | 4/2006 | Borsook et al. | 600/425 |
| 2006/0079495 A1 * | 4/2006 | Blum | 514/184 |
| 2006/0094924 A1 * | 5/2006 | Riehl | 600/9 |
| 2006/0100671 A1 * | 5/2006 | Ridder | 607/45 |
| 2006/0106430 A1 * | 5/2006 | Fowler et al. | 607/45 |
| 2006/0206169 A1 * | 9/2006 | Schuler | 607/58 |
| 2006/0212090 A1 * | 9/2006 | Lozano et al. | 607/45 |
| 2006/0212091 A1 * | 9/2006 | Lozano et al. | 607/45 |
| 2006/0259077 A1 * | 11/2006 | Pardo et al. | 607/2 |
| 2007/0027498 A1 * | 2/2007 | Maschino et al. | 607/45 |
| 2007/0067004 A1 * | 3/2007 | Boveja et al. | 607/45 |
| 2007/0135871 A1 * | 6/2007 | Lipov | 607/89 |
| 2007/0173802 A1 * | 7/2007 | Keppel | 606/34 |
| 2007/0203521 A1 * | 8/2007 | Dobak et al. | 607/2 |
| 2007/0244520 A1 * | 10/2007 | Ferren et al. | 607/2 |
| 2007/0255379 A1 * | 11/2007 | Williams et al. | 607/120 |

FOREIGN PATENT DOCUMENTS

| | | |
|---|---|---|
| WO | WO-93/02743 | 2/1993 |
| WO | WO-98/37926 | 9/1998 |
| WO | WO-98/43700 | 10/1998 |
| WO | WO-98/43701 | 10/1998 |
| WO | WO-01/60450 | 8/2001 |

OTHER PUBLICATIONS

Ahren, et al., "Sympathetic Nerve Stimulation Versus Pancreatic Norepinephrine Infusion in the Dog: 1. Effects on Basal Release of Insulin and Glucagon", Endocrinology, vol. 121, No. 1, (Jul. 1987) pp. 323-331.

Bereiter, et al., "CNS Modulation of Pancreatic Endocrine Function Multiple Modes of Expression", Diabetologia. Suppl. 20, (Mar. 1981) pp. 417-425.

Berthoud, et al., "Characteristics of Gastric and Pancreatic Responses to Vagal Stimulation with Varied Frequencies: Evidence for Different Fiber Calibers?", Journal of the Autonomic Nervous System, vol. 19, No. 1 (Apr. 1987) pp. 77-84.

Berthoud, et al., "Localization of Vagal Preganglionics that Stimulation Insulin and Glucagon Secretion", AM J Physiol, vol. 258, No. 1 Part 2, (Jan. 1990) pp. R160-R168.

Bluher, et al., "Improvement of Insulin Sensitivity After Adrenalectomy in Patients withPheochromocytoma", Diabetes Care, vol. 23, No. 10, (Oct. 1, 2000) pp. 1591-1592.

Brobeck, Jr., "Mechanism of Development of Obesity in Animals with Hypothalamic Lesions", Physiol Rev, vol. 26, (1946) pp. 541-559.

Broglio, et al., "Ghrelin, a Natural GH Secretagogue Produced by the Stomach, Induces Hyperglycemia and Reduces Insulin Secretion in Humans", The Journal of Clinical Endocrinology & Metabolism, vol. 86, No. 10, (Oct. 2001) pp. 5083-5086.

Cameron, et al. "Micromodular Implants to Provide Electrical Stimulation of Paralyzed Muscles and Limbs", IEEE Transactions on Biomedical Engineering, vol. 44, No. 9, (Sep. 1997) pp. 781-790.

Davalli, et al., "Abnormal Sensitivity to Glucose of Human Islets Cultered in a High Glucose Medium: Partial Reversibility After an Additional Culture in a Normal Glucose Medium", Journal of Clinical Endocrinology and Metabolism, vol. 72, (1991) pp. 202-208.

DeNicola, et al., "Abnormal Regulation of Adrenal Function in Rats with Streptozotocin Diabetes", Horm Metab Res, vol. 9, (1977) pp. 469-473.

Dhillo, et al., "Hypothalami Peptides as Drug Targets for Obesity", Current Opinion in Pharmacology, vol. 1, No. 6, (2001) pp. 651-655.

Frankish, et al., "Neuropeptide Y, the Hypothalamus, and Diabetes: Insights Into the Central Control of Metabolism", Peptide, vol. 16, No. 4, (1995) pp. 757-771.

Gardemann, et al., "Reinnervation of Pancreatic Islets and Regulation of Insulin Secretion by Hepatic Sympathetic Nerves After Intrportal Transplantation of Islets Into Livers of Diabetic Rats", Experimental and Clinical Endocrinology and Diabetes, vol. 103, Suppl. 2, (1995) pp. 107-111.

Holst, et al., "Nervous Control of Pancreatic Endocrine Secretion in Pigs. 1. Insulin and Glucagon Responses to Electrical Stimulation of the Vagus Nerves", Acta Physiol Scand, vol. 111, No. 1, (Jan. 1981) pp. 1-7.

Hyde, et al., "Effects of Area Postrema Caudal Medial Nucleus of Solitary Tract Lesions on Food Intake and Body Weight", AM J Physiol, vol. 244, (1983) pp. R577-R587.

Ionescu, et al., "Increases in Plasma Insulin Levels in Response to Electrical Stimulation of the Dorsal Motor Nucleus of the Vagus Nerve", Endocrinology, vol. 112, No. 3, (Mar. 1983) pp. 904-910.

Jonkers, et al., "Influence of Cell Number on the Characteristics and Synchrony of Ca2+ Oscillations in Clusters on Mouse Pancreatic Islet Cells", Journal of Physiology, vol. 520, Part 3, (Nov. 1999) pp. 839-849.

Kakizaki, et al., "Neural Regulation of Auto-Grafted Islets of Langerhans", Nippon Geka Gakkai Zasshi, vol. 89, No. 3, (Mar. 1988) pp. 394-397.

Kakizaki, et al., "Neutral Regulation of Heterotopic Islets of Langerhans", Surgery, vol. 100, No. 6, (Dec. 1986) pp. 997-1002.

Kurose, et al., "Glucagon, Insulin and Somatostatin Secretion in Response ot Sympathetic Neural Activation in *Spreptozotocin*-Induced Diabetic Rats. A study with the Isolated Perfused Rat Pancreas in Vitro", Diabetologia, vol. 35, No. 11, (Nov. 1992) pp. 1035-1041.

Kurose, et al., "Mechanism of Sympathetic Neural Regulation of Insulin, Somatostatin, and Glucagon Secretion", Am J Physiol, vol. 258, No. 1, part 1, (Jan. 1990) pp. E220-E227.

Lorrain, et al., "Adrenergic and Nonadrenergic Cotransmitters Inhibit Insulin, Secretion During Sympathetic Stimulation in Dogs", AM J Physiol, vol. 263, No. 1 Part 1. (Jul. 1992) pp. E72-E78.

Mayfield, et al., "A Role for the Agouti-Related Protein Promoter in Obesity and Type 2 Diabetes", Biochemical and Biophysical Research Communications, vol. 287, No. 2, (Sep. 21, 2001) pp. 568-573.

Minami, et al., Electrophysiological Properties and Glucose Responsiveness of Guinea-pig Ventromedial Hypothalamic Neurons in Vitro, J Physiol, vol. 380, (1986) pp. 127-143.

Misler, et al., "Electrophysiology of Stimulus-Secretion Coupling in Human Beta-Cells", Diabetes, vol. 41, No. 10, (Oct. 1992) pp. 1221-1228.

Mondal, et al., "Orexins (hypocretins): Novel Hypothalami Peptides with Divergent Functions", Biochem Cell Biol, vol. 78, (2000) pp. 299-305.

Nakazato, et al., "A Role for Ghrelin in the Central Regulation of Feeding", Nature, vol. 409, No. 6817, (Jan. 11, 2001) pp. 194-198.

Nishi, et al., Vagal Regulation of Insulin, Glucagon, and Somatostatin in Vitro in the Rat, J Clin Invest, vol. 79, No. 4, (Apr. 1987) pp. 1191-1196.

Oomura, et al., "Gluose and Osmosensitive Neurons of the Rat Hypothalamus", Nature, vol. 222, (1969) pp. 282-284.

Perkins, et al., "Activation of Brown Adipose Tissue Thermogenesis by the Ventromedial Hypothalamus", Nature, vol. 289, (Jan. 1981) pp. 401-402.

Pierroz, et al., "Chronic Administration of Neuropeptide Y Into the Lateral Ventricle Inhibits Both the Pituitary-Testicular Axis and Growth Hormone and Insulin-Like Growth Facter I Secretion in intact Adult Male Rats", Endrodinology, vol. 137, No. 1, (Jan. 1996) pp. 3-12.

Pi-Sunyer, Pathogenesis of Obesity, Drug Benefit Trends, vol. 12, Supp A, (2002) pp. 28-33.

Qu, et al., "Agouti-Related Protein is a Mediator of Diabetic Hyperphagia", Regulatory Peptides, vol. 98, No. 1-2, (Apr. 2, 2001) pp. 69-75.

Ratner, "Innovations in Managing Type 2 Diabetes", Drug Benefit Trends, vol. 12, Supp A, (2000) pp. 34-43.

Ravier, et al., "Oscillations of insulin Secretion Can be Triggered by Imposed Oscillations of Cytoplasmic Ca2+ or Metabolism in Normal Mouse Islets", Diabetes, vol. 48, No. 12, (Dec. 1999) pp. 2374-2382.

Sahu, et al., "Evidence that Neurotensin Mediates the Central Effect of Leptin on Food Intake in Rat", Brain Research, vol. 888, No. 2, (Jan. 12, 2001) pp. 343-347.

Sawchenko, et al., "The Distrisbution of Cells of Organ of Serotonin Input to the Paraventricular and Supraoptic Nuclei of the Rat", Brain Research, vol. 277, (1983) pp. 355-360.

Shor-Posner, et al., "Deficits in the Control of Food Intake After Paraventricular Nucleus Lesions", Physiology and Behavior, vol. 35, (1985) pp. 883-890.

Tanaka, et al., "Effects of Intraventricular Administration of Neuropeptide Y on Feeding Behavior in Fasted Female Rats with Ventromedial Hypothalamic Lesions", Regulatory Peptides, vol. 52, No. 1, (Jun. 16, 1994) pp. 47-52.

Thomas, et al., "Reversal of Type II (NIDDM) Diabetes by Pancreas Islet Transplantation: an Emerging New Concept in Pathophysiology of an Enigmatic Disease", Transplantation Proceedings, vol. 27, No. 6, (Dec. 1995) pp. 3167-3169.

Zaborsky, et al., "Brainstem Projection to the Hypothalamic Paraventricular Nucleus in the Rat, a CCK-Containing Long Ascending Pathway", Brain Research, vol. 303, (1984) pp. 225-231.

"Hormones Found in the Brain May Determine How Much You Eat and Affect Obesity and Diabetes", printed Dec. 12, 2002, pp. 1-2.

"Neurogen Commences Phase 1b Human Clinical Trials with Anti-Obesity Drug", printed Dec. 6, 2002, p. 1.

"Obesity: Mechanism: Neuropeptide Y Receptor Antagonists", Neurogen Corporation, printed Aug. 21, 2002, pp. 1-2.

Wahlestedt, et al. "Neuropeptide Y and Related Peptides", printed Jul. 10, 2001, pp. 1-10.

Wells, William A., "Possible Finding on Weight Control", Stanford online Report, printed Dec. 9, 2002, pp. 1-3.

Clore Laboratory: News Diabetes, Obesity and Metabolic Research, "Jun. 7, 2001—Hot topic poster European Obesity Congress", printed Dec. 12, 2002, p. 1.

Whitehurst inventor for AB-145U; U.S. Appl. No. 09/993,085, filed Nov. 6, 2001; entitled "Systems and Methods for Treatment of Diabetes by Electrical Brain Stimulation and/or Drug Infusion". (Other Prior Art—Related Application).

Whitehurst and McGivern inventors for AB-147U; U.S. Appl. No. 09/993,084, filed Nov. 6, 2001; entitled "Systems and Methods for Modulation of Pancreatic Endocine Secretion and Treatment of Diabetes". (Other Prior Art—Related Application).

Ahn, et al. "Modulation by Central and Basolateral Amygdalar Nuclei of Dopaminergic Correlates of Feeding ot Satiety in the Rat Nucleas Accumbens and Medial Prefrontal Cortex", The Journal of Neuroscience, vol. 22, No. 24, (Dec. 15, 1995) pp. 10958-10965.

Critchley, et al. "Hunger and Satiety Modify the Responses of Olfactory and Visual Neurons in the Primate Orbitofrontal Cortex", Journal of Neurophysiology, vol. 75, No. 3 (Apr. 1996) pp. 1673-1686.

Gordon, et al. "Neuroanatomy of Human Appetitive Function: a Positron Emission Tomography Investigation", John Wiley & Sons, Prod. #1480 (2000).

Hellstrom, et al. "Peripheral and central signals in the control of eating in normal, obese and bing-eating human subjects", British Journal of Nutrition, vol. 92, Suppl 1, (2004) pp. S47-S57.

Hinton, et al. "Neural contributions to the motivational control of appetite in humans", European Journal of Neuroscience, vol. 20, (2004) pp. 1411-1418.

Morton, et al. "Leptin action in the forebrain regulates the hindbrain response to satiety signals", The Journal of Clinical Investigation, vol. 115, No. 3 (Mar. 2005) pp. 703-710.

Ongur, et al. "The Organization of Networks within the Orbital and Medial Prefrontal Cortex of Rat, Monkeys and Humans", Cerebral Cortex vol. 10, No. 3 (Mar. 2000) pp. 206-219.

Parigi, et al. "Neuroimaging and Obesitya: Mapping the Brain Responses to Hunger and Satiation in Humans Using Positron Emission Tomography", Ann. N.Y. Acad. Sci. vol. 967 (2002) pp. 389-397.

Pelchat, et al. "Images of desire: food-craving activation during fMRI", NeuroImage, vol. 23 (2004) pp. 1486-1493.

Rolls, et al. "Responses to the Sensory Properties of Fat of Neurons in the Primate Orbitofrontal Cortex", The Journal of Neuroscience, vol. 19, No. 4 (Feb. 15, 1999) pp. 1532-1540.

Small, et al. "Feeding-induced dopamine release in dorsal striatum correlates with meal pleasantness ratings in healthy human volunteers", NeuroImage, vol. 19 (2003) pp. 1709-1715.

Stamatakis, et al. "Neuroimaging in Eating Disorders", Nutritional Neuroscience, vol. 6, No. 6 (Dec. 2003) pp. 325-334.

Sutton, "Functional Neuroanatomy", University of Derby, Brain & Behaviour Level V 5SP021 (Spring 2005).

Tataranni, et al. "Neuroanatomical correlates of hunger and satiation in humans using positon emission tomography", Proc. Natl. Acad. Sci., vol. 96, (Apr. 1999) pp. 4569-4574.

Wang, et al. "Exposure to appetitive food stimuli marked activities the human brain", NeuroImage, vol. 21 (2004) pp. 1790-1797.

* cited by examiner

TREATMENT OF PATHOLOGIC CRAVING AND AVERSION SYNDROMES AND EATING DISORDERS BY ELECTRICAL BRAIN STIMULATION AND/OR DRUG INFUSION

CROSS REFERENCE TO RELATED APPLICATIONS

This application claims priority as a continuation-in-part of U.S. patent application Ser. No. 09/993,086, filed Nov. 6, 2001 and published as US2005/0033376, which claims priority based on U.S. Provisional Patent Application Ser. No. 60/252,625, filed Nov. 21, 2000, which applications are incorporated herein by reference in their entirety.

FIELD OF THE INVENTION

The present invention generally relates to drug delivery and electrical stimulation systems and methods, and more particularly relates to utilizing one or more devices to deliver electrical stimulation and/or one or more stimulating drugs to certain areas of the brain as a treatment for pathological craving and aversion syndromes including drug addiction, smoking, alcoholism, as well as obesity and eating disorders.

BACKGROUND OF THE INVENTION

A number of different physiologic states are either directly or tangentially related to the desire to consume food and thus attain a feeling of satiation. Obesity affects millions of Americans, and a substantial percentage of these people are morbidly obese, suffering such obesity-related problems as heart disease, vascular disease, and social isolation. An additional number of Americans suffer from various other eating disorders that may result in cachexia (i.e., a general physical wasting and malnutrition) or periods of obesity and/or cachexia. The etiology of obesity is largely unknown. The etiology of some eating disorders is psychological in many patients, but for other patients, is poorly understood.

Both obesity and its effective counterparts, anorexia and bulimia, are affected by both food intake and metabolic demand, including by exercise, basal metabolism and thermogenesis. These are in turn influenced by the combined effects of genetics and metabolic efficiency. Satisfactory treatments for orexic or appetite related conditions including obesity and anorexia remain elusive.

Patients suffering from morbid obesity and/or other eating disorders have very limited treatment options. For instance, some of these patients may undergo surgery to reduce the effective size of the stomach ("stomach stapling") and to reduce the length of the nutrient-absorbing small intestine. Such highly invasive surgery is associated with both acute and chronic complications, including infection, digestive problems, and deficiency in essential nutrients. In extreme cases, patients may require surgical intervention to a put a feeding tube in place. Patients suffering from obesity and eating disorders (ED) may suffer long-term complications such as osteoporosis and irreversible changes in brain morphology and function. Additional treatment options are needed.

Likewise, pathological conditions related to craving including drug addiction, nicotine addiction and alcohol addiction severely affect a significant portion of the population. Studies have shown that once addicted, failure rates for nicotine, heroin and alcohol addiction are the same with 70% relapsing within a year after abstaining. These pathological craving conditions are obviously not readily treated by existing therapies.

BRIEF SUMMARY OF THE INVENTION

The invention disclosed and claimed herein provides systems and methods for introducing one or more stimulating drugs and/or applying electrical stimulation to one or more areas of the brain for treating or preventing obesity and/or other eating disorders, as well as addiction. Proper stimulation of specific sites in the brain via Deep Brain Stimulation (DBS) may lead to changes in levels or responses to neurotransmitters, hormones, and/or other substances in the body that affect hunger, craving and satiation.

In one embodiment of the invention, one or more system control units (SCUs) apply electrical stimulation and/or one or more stimulating drugs to one or more predetermined stimulation sites in the brain, for instance, to an appropriate area of the hypothalamus. In some forms of an SCU, one or more electrodes are surgically implanted to provide electrical stimulation from an implantable signal/pulse generator (IPG) and/or one or more infusion outlets and/or catheters are surgically implanted to infuse drug(s) from an implantable pump. In other forms of an SCU, a miniature implantable neurostimulator (a.k.a., a microstimulator, such as a BION® microstimulator of Advanced Bionics Corporation of Valencia, Calif.), is implanted. Some forms of the disclosed systems also include one or more sensors for sensing symptoms or conditions that may indicate a needed treatment.

An SCU may provide both electrical stimulation and one or more stimulating drugs when necessary and/or desired. In some embodiments, the SCU is implanted in a surgically-created shallow depression or opening in the skull, such as in the temporal, parietal, or frontal bone. In some such embodiments, one or more electrode leads and/or catheters attached to the SCU run subcutaneously to an opening in the skull and pass through the opening into or onto the brain parenchyma and surrounding tissue. In other embodiments, the SCU is remote from the brain and communicates electrically and/or via conduits to the area of the brain to be stimulated.

Patients with an eating disorder or pathological craving syndrome such as drug, alcohol or nicotine addiction will likely respond to therapeutic excitatory stimulation applied to those areas of the brain that exhibit chronic decreased activity relative to normal control subjects. Thus, according to certain embodiments of the invention, the stimulation increases excitement of one or more of those areas of the brain that exhibit chronic decreased activity in patients relative to normal control subjects, thereby treating or preventing eating disorders or pathological craving syndrome and/or the symptoms and/or consequences thereof. Such excitatory stimulation is likely to be produced by, for example, low-frequency electrical stimulation, an excitatory neurotransmitter agonist, and/or an excitatory hormone agonist. Additional potential (but not necessary) uses of the present invention include, but are not limited to, treatment for and prevention of diabetes and other conditions caused or worsened by eating disorders, via the promotion of normal metabolism and weight control, as well control of pathological craving syndromes.

Patients with an eating disorder or pathological craving syndrome such as drug, alcohol or nicotine addiction will likely respond to therapeutic inhibitory stimulation applied to those areas of the brain that exhibit chronic increased activity relative to normal control subjects. Thus, according to various embodiments of the invention, the stimulation decreases excitement of one or more of those areas of the brain that exhibit chronic increased activity in patients relative to normal control subjects, thereby treating or preventing eating disorders, pathological craving syndromes, and/or the symptoms and/or consequences thereof. Such inhibitory stimulation is likely to be produced by, for example, high-frequency electrical stimulation, an inhibitory neurotransmitter agonist, and/or an inhibitory hormone agonist. Again, additional potential (but not necessary) uses include, but are not limited to, treatment for and prevention of conditions caused or worsened by eating disorders, via the promotion of normal metabolism and weight control, as well control of pathological craving syndromes.

The SCU may include a programmable memory for storing data and/or control parameters. This allows stimulation and control parameters to be adjusted to levels that are safe and efficacious with minimal discomfort. Electrical and drug stimulation may be controlled independently; alternatively, electrical and drug stimulation may be coupled, e.g., electrical stimulation may be programmed to occur only during drug infusion.

According to some embodiments of the invention, the electrodes used for electrical stimulation are arranged as an array on a thin implantable lead. In other embodiments the electrodes are arranged as a two dimensional array of thin implantable leads. In one embodiment the array is disposed in an implantable mesh. A variety of other lead and electrode designs may be used with the invention, including paddle, cuff, and thin wire electrodes, and electrodes on the surface of a leadless SCU. The SCU may be programmed to produce either monopolar electrical stimulation, e.g., using the SCU case as an indifferent electrode, or bipolar electrical stimulation, e.g., using one of the electrodes of the electrode array as an indifferent electrode. The SCU may include a means of stimulating a nerve or infusing a stimulating drug(s) either intermittently or continuously. Specific stimulation/infusion parameters may provide therapy for, e.g., varying types and degrees of severity of eating disorders.

The SCU used with one embodiment of the present invention possesses one or more of the following properties, among other properties:
 at least one electrode for applying stimulating current to surrounding tissue and/or a pump and at least one outlet for delivering a drug or drugs to surrounding tissue;
 electronic and/or mechanical components encapsulated in a hermetic package made from biocompatible material(s);
 an electrical coil inside the package that receives power and/or data by inductive or radio-frequency (RF) coupling to a transmitting coil placed outside the body, avoiding the need for electrical leads to connect devices to a central implanted or external controller;
 telemetry circuitry for receiving and/or transmitting signals;
 receiving and/or electrical power storage circuitry within the SCU; and
 a form factor making the SCU implantable in a depression or opening in the skull, or within the brain.

The power source of the SCU is realized using one or more of the following options, or the like:
 (1) an external power source coupled to the SCU via a radio-frequency (RF) link;
 (2) a self-contained power source for generation or storage of energy, e.g., a primary battery, a replenishable or rechargeable battery, a capacitor, a supercapacitor; and/or
 (3) if the self-contained power source is replenishable or rechargeable, replenishing or recharging the power source can be provided by an RF link, an optical link, or other energy-coupling link.

According to certain embodiments of the invention, an SCU operates independently. According to various embodiments of the invention, an SCU operates in a coordinated manner with other implanted SCUs, other implanted devices, or with devices external to the patient's body.

According to several embodiments of the invention, an SCU incorporates modalities of sensing the disorder or symptoms thereof, or other measures of the state of the patient. Sensed information may be used to control the electrical and/or drug stimulation parameters of the SCU in a closed loop manner. According to some embodiments of the invention, the sensing and stimulating modalities are incorporated into a single SCU. According to several embodiments of the invention, the sensing modalities communicate sensed information to at least one SCU with stimulating modality.

In one embodiment of the invention a method of treating a pathological craving or aversion syndrome in a patient so afflicted is provided that includes implanting one or more system control units in the patient, wherein one or more of the system control units are connected to and control one or more electrodes and/or drug delivery catheters that are implanted in the brain of the patient and control delivery of a stimulus to one or more brain areas that control hunger or satiation. The brain areas that control hunger or satiation include the nucleus of the solitary tract, ventromedial nucleus of the hypothalamus (VMH), arcuate nucleus of the hypothalamus (ARC), paraventricular nucleus of the hypothalamus (PVN), lateral nucleus of the hypothalamus (LHA), ventral tegmental area (VTA), nucleus accumbens (NAc), amygdala, insula cortex, medulla, ventral striatum, caudate, thalamus, orbitofrontal cortex, anterior cingulate cortex, putamen, hippocampal and parahippocampal formations, prefrontal cortex, inferior parietal lobe, temporal cortex, and combinations thereof.

In some examples, the prefrontal cortex stimulus is applied to at least one of the ventromedial prefrontal cortex and the dorsolateral prefrontal cortex and the stimulus to the orbitofrontal cortex, insula cortex, putamen or amygdala is applied to at least an area of the right orbitofrontal cortex, anterior insula, dorsal putamen, and basolateral amygdala (BLA).

In a further embodiment, the system control unit is connected to at least one pump and at least one infusion outlet, and the stimulus comprises stimulation via one or more drugs delivered from the pump through the outlet.

In one embodiment of the invention the pathological craving syndrome is associated with food and has resulted in obesity and wherein the stimulus is applied to at least one of the ventral tegmental area (VTA), nucleus accumbens (NA), hippocampus, anterior insula, caudate, superior temporal, and right orbitofrontal cortices. In another embodiment, the pathological craving syndrome is associated with craving for one or more of an addictive drug, nicotine, and alcohol. In one embodiment, the stimulus is applied to two of more of the areas to prevent accommodation.

One embodiment of the invention provides for electrical stimulation and measured response of the individual patient, followed by tuning and controlling of the electrical stimulation by customized programming. The system control unit in one embodiment is connected to a plurality of electrodes disposed in an electrode array that is particularly advantageous for stimulus to areas of the brain that are activated in hunger and satiation but are variously located across a relatively large of the brain due to variability between individuals in the fine architecture of specific control and response regions of their brains.

In one embodiment of the invention a method of treating a patient having an eating disorder, including both over and undereating and food aversion is provided that includes electronically sensing at least one condition indicating a need for stimulus to one or more areas of the brain that is active in hunger and satiation by a sensor that sends an electronic signal to at least one system control unit, thereby activating the system control unit, the system control unit then activates one or more electrodes and/or drug delivery catheters implanted in the brain of the patient to deliver a stimulus to one or more areas of the brain active in hunger and satiation. In one embodiment the sensed condition is at least one of regional cerebral blood flow (rCBF), impedance, pH, electrical activity of the brain, nerve activity, muscle activity, neurotransmitter level, neurotransmitter breakdown product level, hormone level, ketone level, glucose level, electrolyte level, enzyme level, cytokine level, medication level, other drug level, and level of any other bloodborne substance.

In one embodiment, the sensed condition is a differential hemispheric rCBF in the frontal cortex. In another embodiment, the sensed condition is activity in one or more of the temporo-insular cortical, medial temporal lobes, supplementary motor area, somatosensory cortex, cerebellum, anterior cingulated and orbitofrontal cortex (OFC).

In a further embodiment, an implanted system includes a system control unit and at least one pump and at least one infusion outlet that are configured to deliver a compound that increases or decreases excitement of at least one area of the brain that exhibits chronic increased or decreased activity in the patient. In one embodiment the compound is one or more of at least one of an excitatory neurotransmitter agonist, a medication that increases levels of at least one excitatory neurotransmitter, an excitatory hormone agonist, an inhibitory neurotransmitter antagonist, an inhibitory hormone antagonist, corticotropin releasing factor, a corticotropin releasing factor agonist, bombesin, a bombesin agonist, glucagon-like peptide 1, a glucagon-like peptide 1 agonist, serotonin, a serotonin agonist, leptin, a leptin agonist, a ghrelin antagonist, an AGRP antagonist, an MC4-R agonist, an MC3-R agonist, an orexin-A antagonist, an orexin-B antagonist, an OX1R antagonist, an OX2R antagonist, cholecystokinin, a cholecystokinin agonist, dopamine, dynorphin, melanin-concentrating hormone, melanocyte-stimulating hormone, growth hormone-releasing hormone (GHRH), endocannobinoids, beta-endorphin, galanin, an inhibitory neurotransmitter agonist, a medication that increases the level of an inhibitory neurotransmitter, an inhibitory hormone agonist, an excitatory neurotransmitter antagonist, and/or an excitatory hormone antagonist.

In one embodiment, a method of modulating the basal metabolic rate in a patient includes implanting one or more system control units in the patient, wherein one or more of the system control units are connected to and control one or more electrodes and/or drug delivery catheters that are implanted in the brain of the patient and control delivery of a stimulus to one or more brain areas that control basal metabolic rate. The stimulus can be delivered to one or more of the hypothalamus, thyroid, pituitary and locus coeruleus. In some examples, the stimulus to the hypothalamus is delivered to the paraventricular nucleus (PVN).

The above and other aspects of the present invention will be more apparent from the following more particular description thereof, presented in conjunction with the following drawings.

BRIEF DESCRIPTION THE DRAWINGS

Figure 3A:
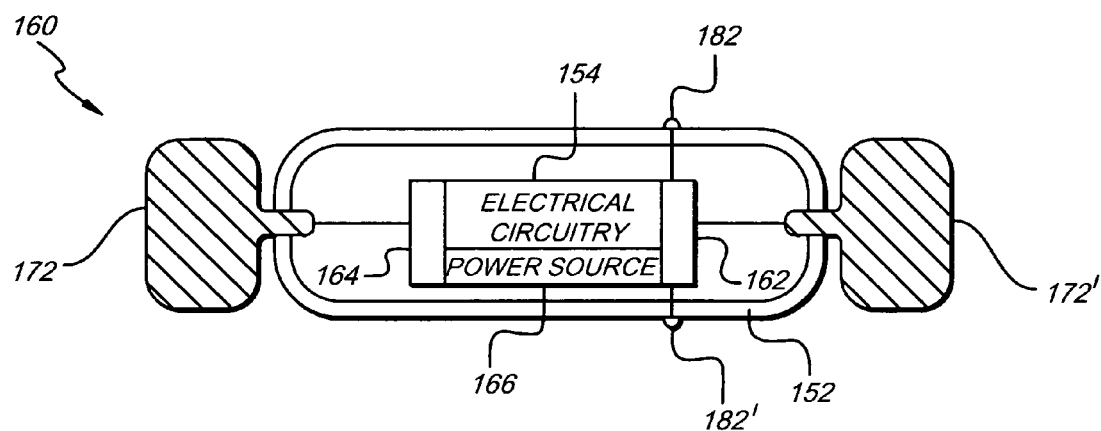
Figure 3B:
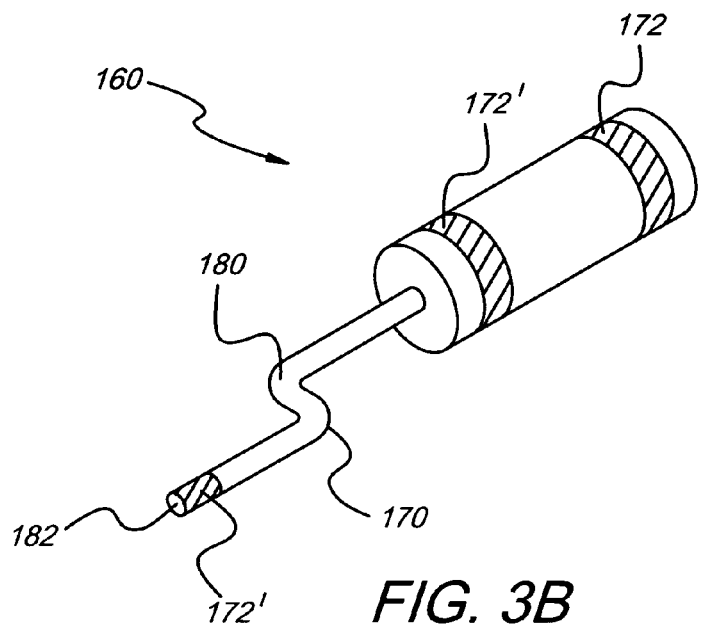
Figure 3C:
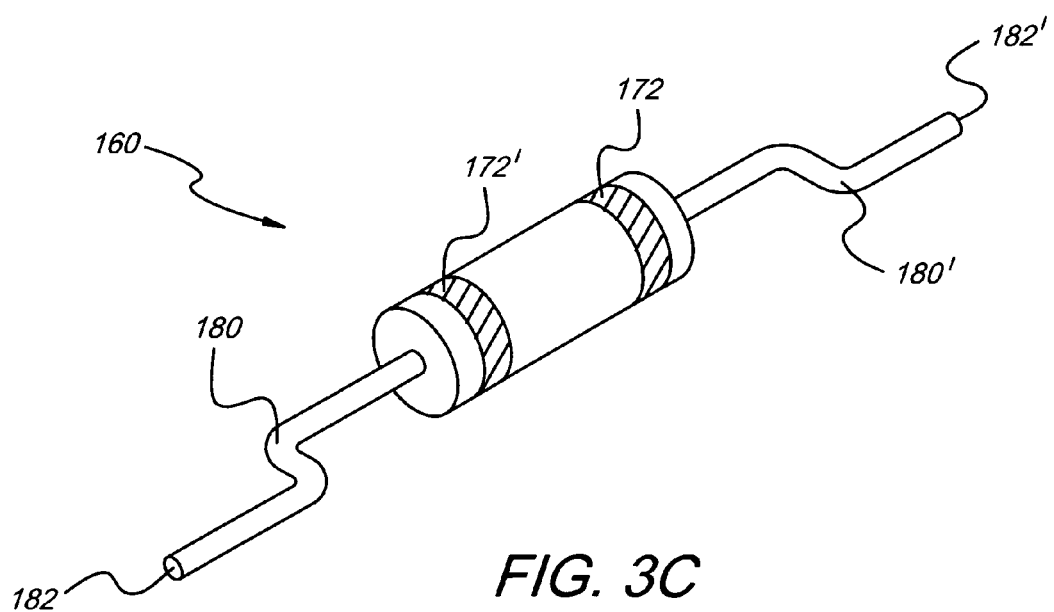

FIGS. 3A, 3B, and 3C show some possible configurations of an implantable microstimulator of the present invention.

Figure 4:
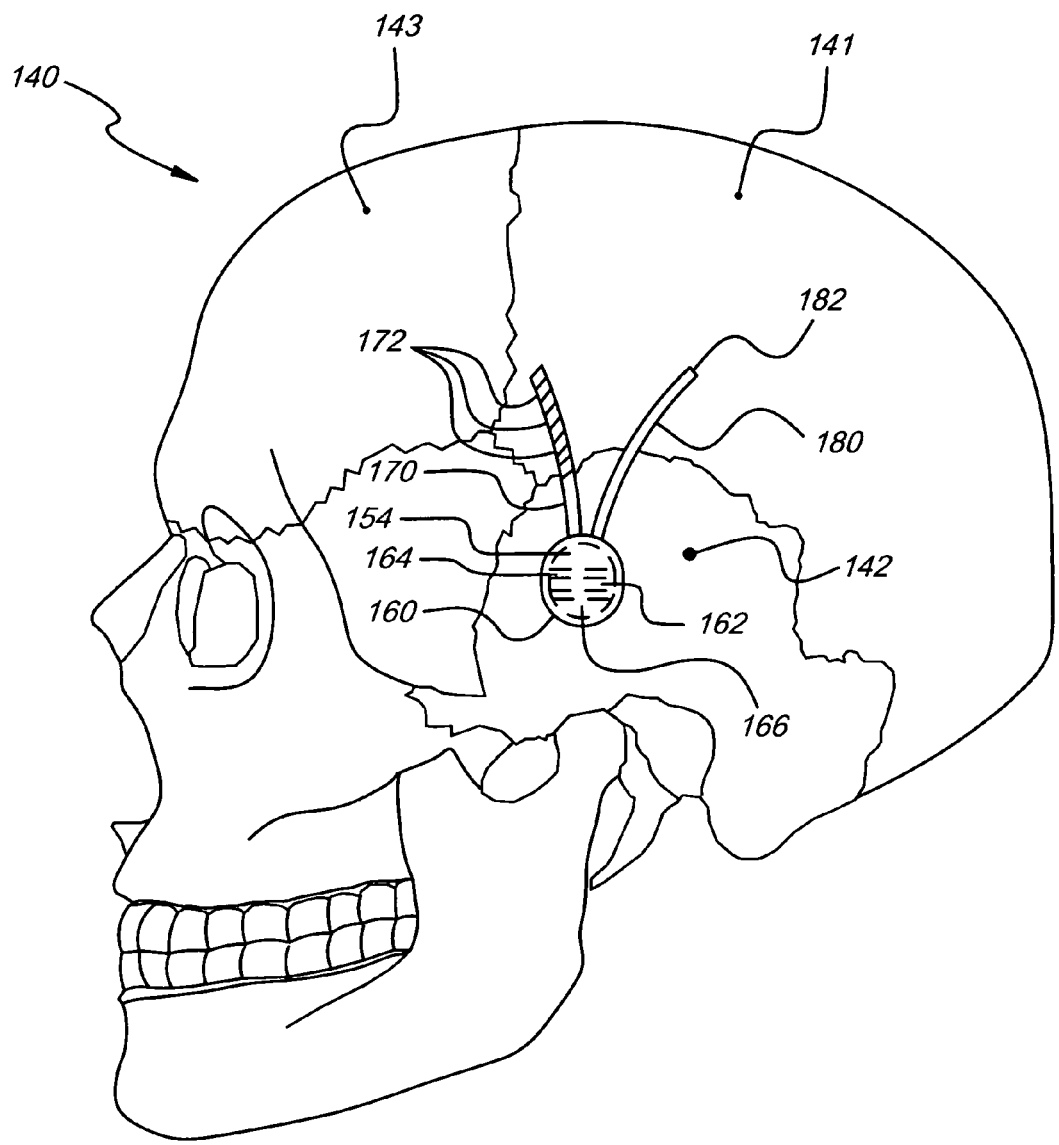

FIG. 4 illustrates a lateral view of the skull and components of some embodiments of the invention.

Figure 5:
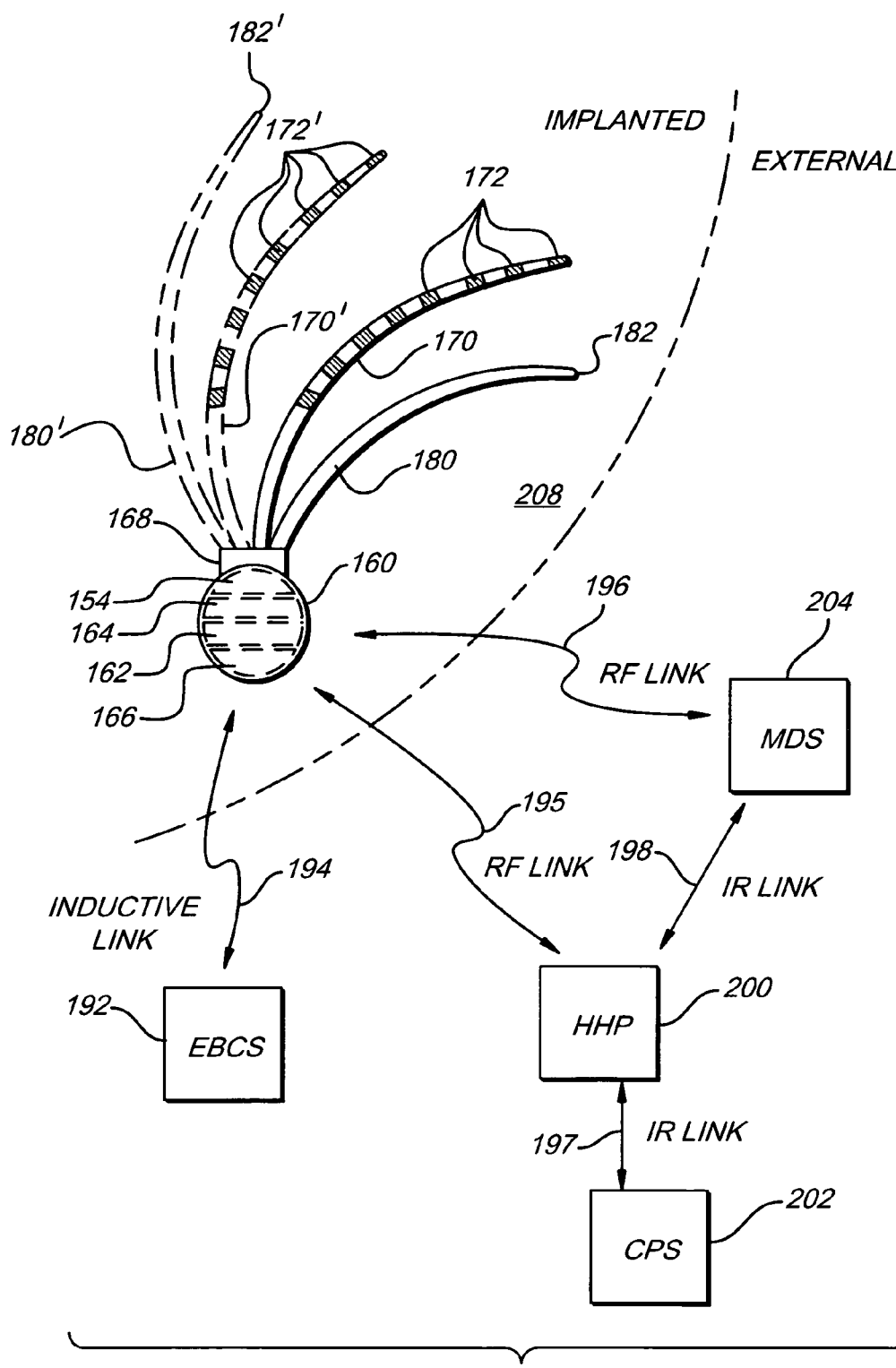

FIG. 5 illustrates internal and external components of certain embodiments of the invention.

Figure 6:
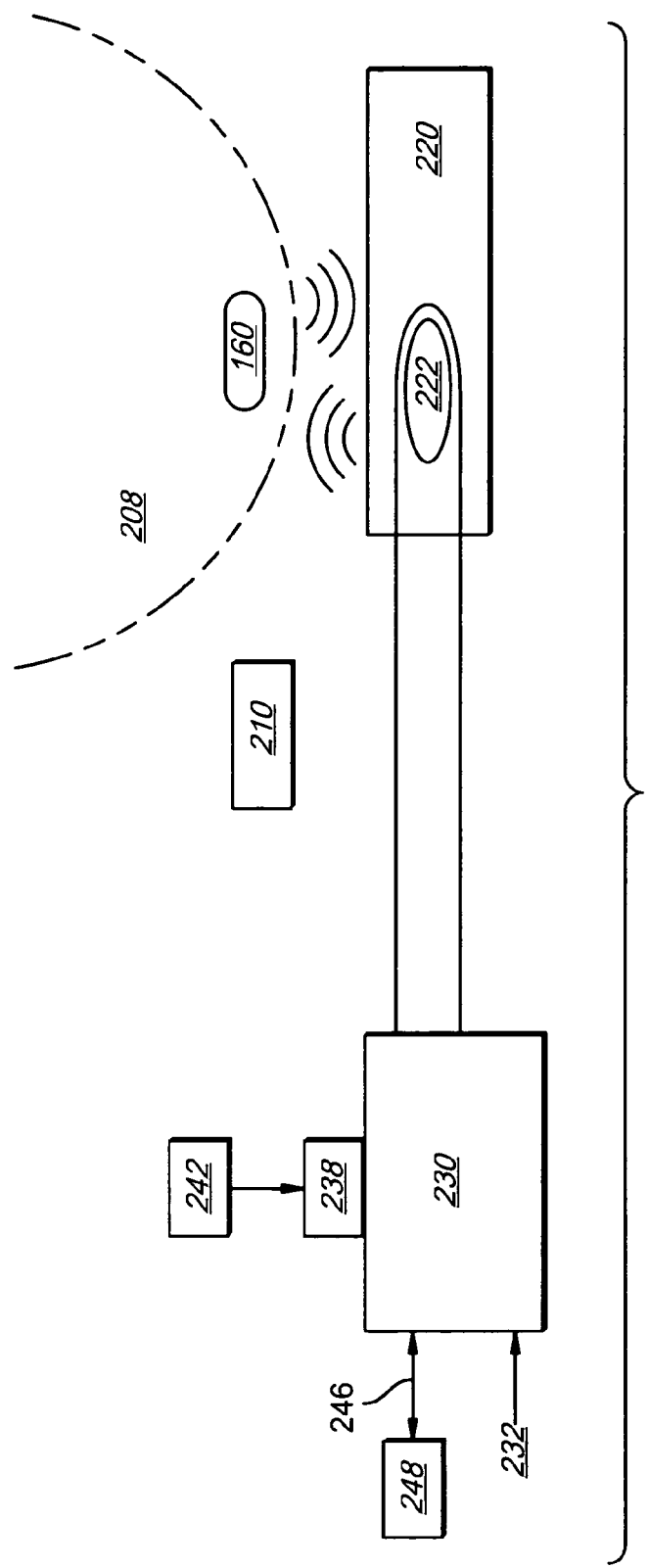

FIG. 6 illustrates external components of various embodiments of the invention.

Figure 7:
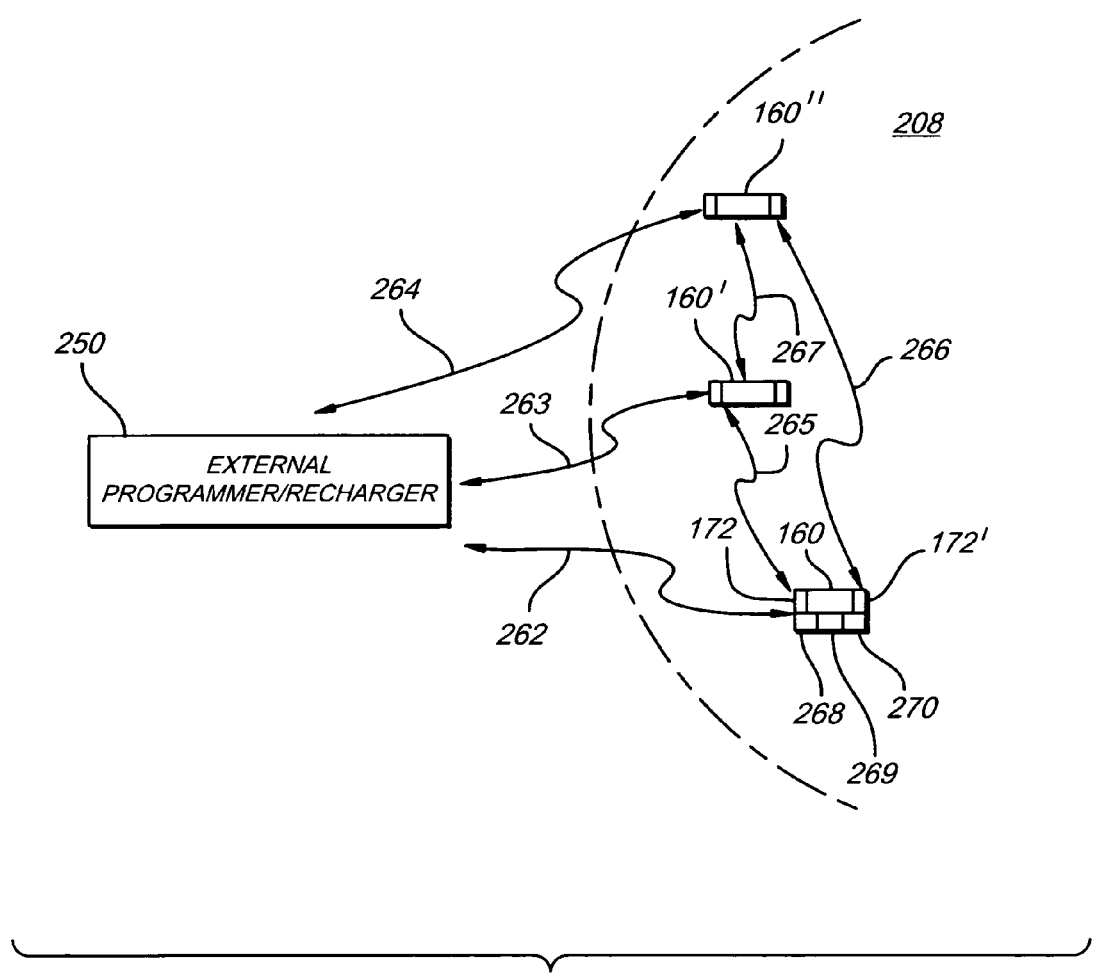

FIG. 7 depicts a system of implantable devices that communicate with each other and/or with external control/programming devices.

Figure 8:
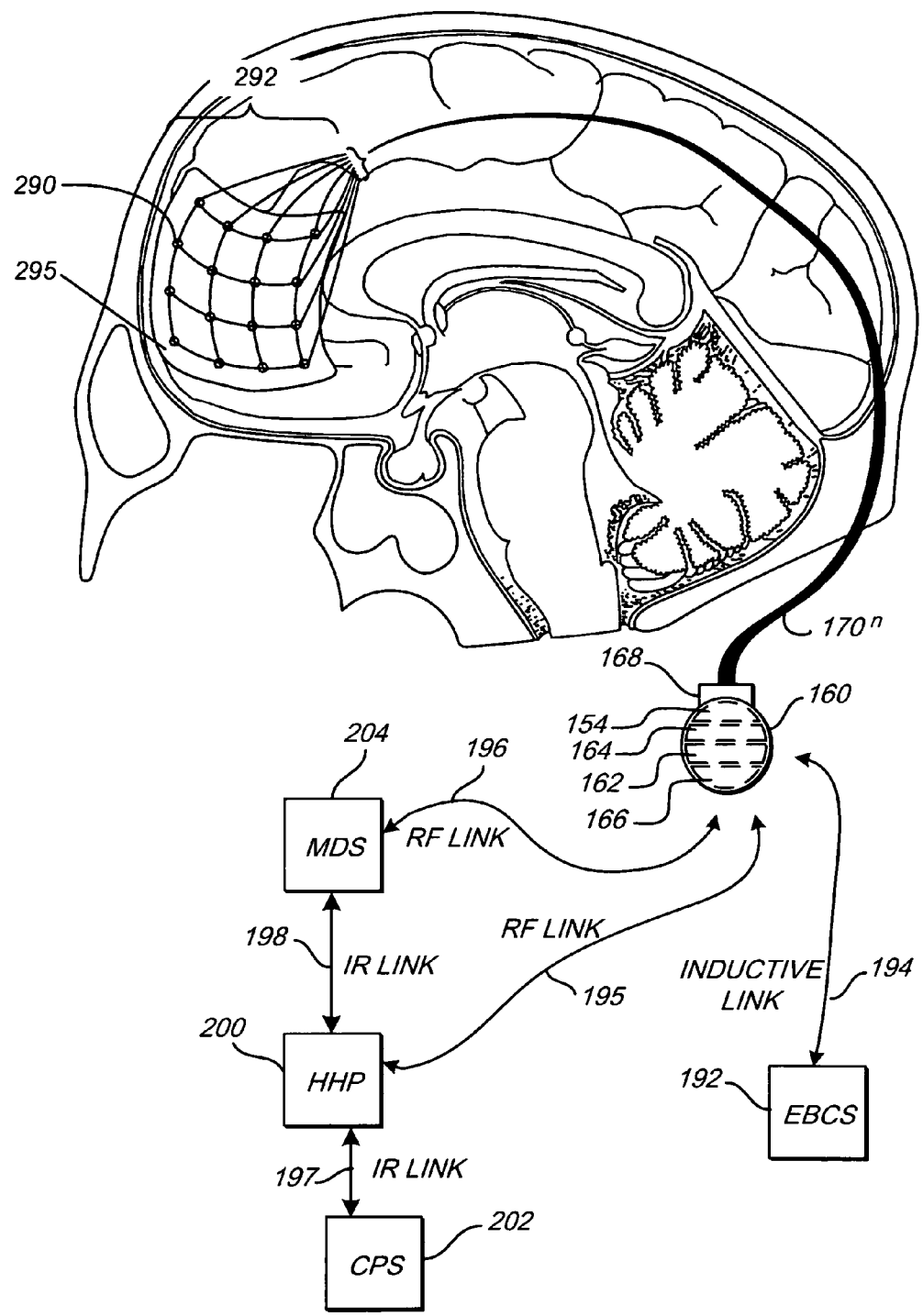

FIG. 8 illustrates an implantable electrode array according to one embodiment of the invention.

Figure 9A:
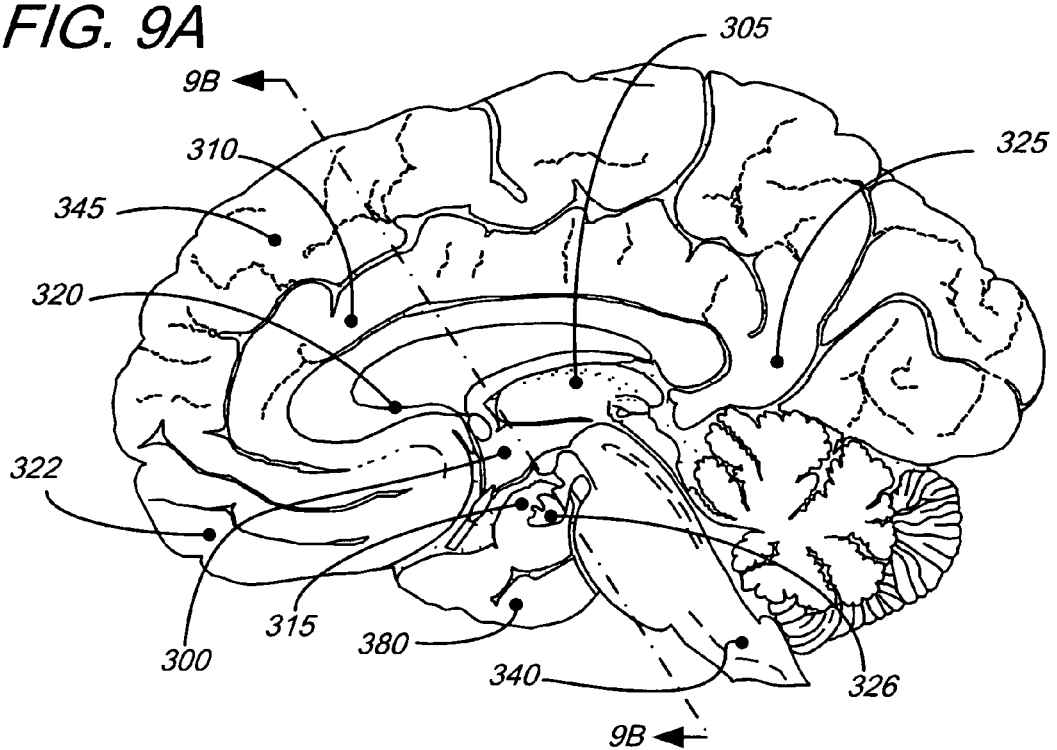

FIG. 9A illustrates lateral view of the brain and locations of some embodiments of the invention.

Figure 9B:
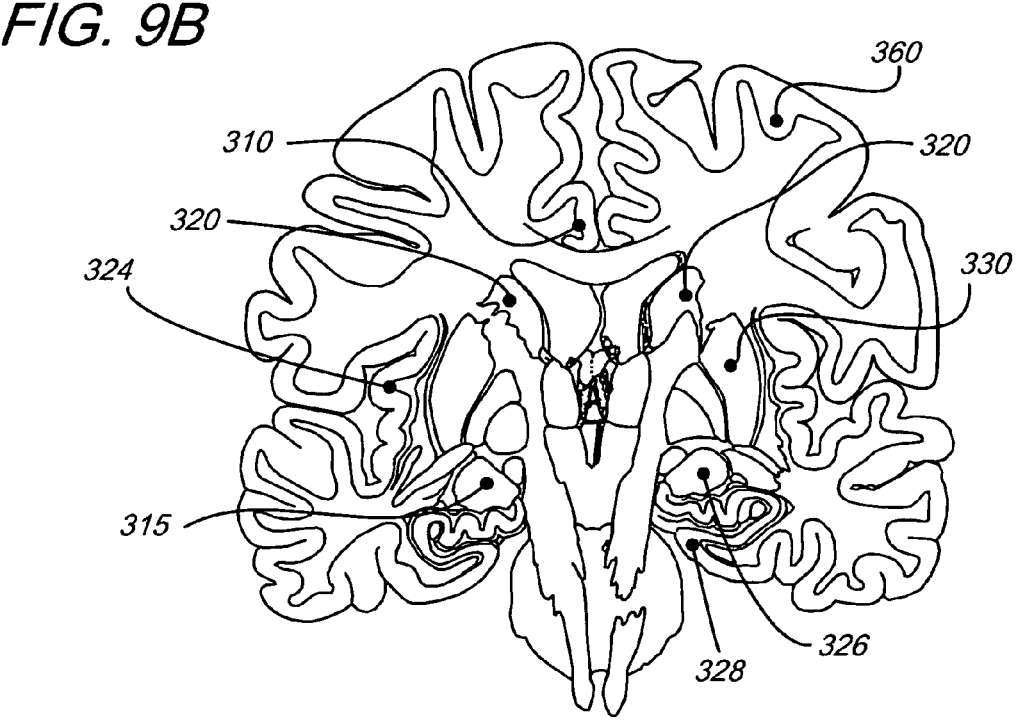

FIG. 9B illustrates a coronal view of one section of the brain from 9A.

Figure 10:
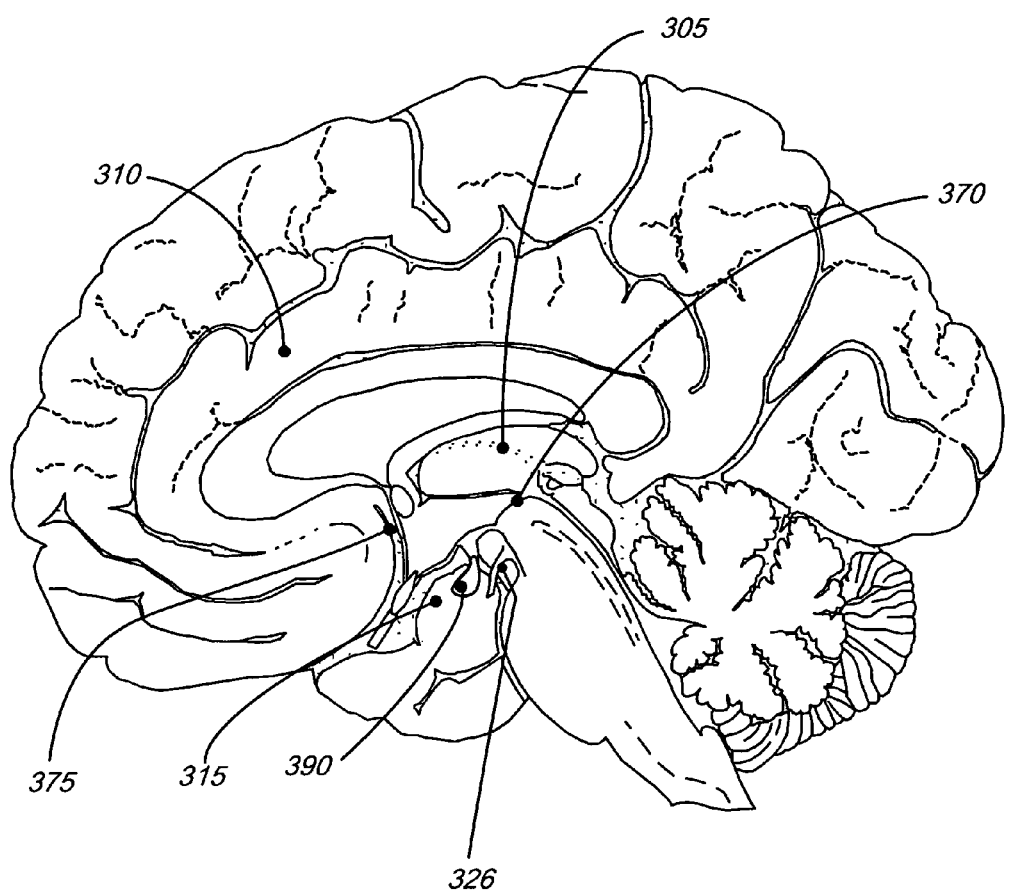

FIG. 10 illustrates a further lateral view of the brain and locations of some embodiments of the invention.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

ABBREVIATIONS: The following mediator and receptor abbreviations are used throughout this application:

| | |
|---|---|
| 5-HT | serotonin |
| ACTH | adrenocorticotrophic hormone |
| ADH | antidiuretic hormone |
| AGRP | Agouti-Related Protein |
| CCK | cholecystokinin |
| CRF | corticotropin releasing factor |
| FSH | follicle-stimulating hormone |
| GABA | gamma-aminobutyric acid |
| GH | growth hormone |
| GHRH | growth hormone-releasing hormone |
| GnRH | gonadotropin-releasing hormone |
| LH | luteinizing hormone |
| LHRH | luteinizing hormone releasing hormone |
| MC3-R | melanocortin 3 receptor |
| MC4-R | melanocortin 4 receptor |
| MSH | melanocyte-stimulating hormone |
| NPY | Neuropeptide Y |
| OX1R | Orexin-A receptor |
| OX2R | Orexin-B receptor |
| TRH | thyrotropin releasing hormone |
| TSH | thyroid stimulating hormone |

The following medical abbreviations are used throughout this application:

| | |
|---|---|
| AN | anorexia nervosa |
| ARC | arcuate nucleus of the hypothalamus |
| BLA | basolateral complex of the amygdala |
| BMI | body mass index |
| BN | bulimia nervosa |
| CING | cingulate cortex |
| CINV | Chemotherapy-Induced Nausea and Vomiting |

-continued

| | |
|---|---|
| CT | computed tomography |
| DMN of Xth nerve | dorsal motor nucleus of the Vagus |
| ED | Eating disorders |
| fMRI | functional MRI |
| LHA | lateral nucleus of the hypothalamus |
| MRI | Magnetic Resonance Imaging |
| NAc | nucleus accumbens |
| OFC | orbitofrontal cortex |
| OVLT | organum vasculosum lamina terminalis |
| PET | positron emission tomography |
| PONV | Post Operative Nausea and Vomiting |
| PRF | prefrontal cortex |
| PVN | paraventricular nucleus of the hypothalamus |
| rCBF | regional cerebral blood flow |
| RINV | Radiation-Induced Nausea and Vomiting |
| SCN | suprachiasmatic nucleus of the hypothalamus |
| SPECT | single photon emission CT |
| VMH | ventromedial nucleus of the hypothalamus or ventromedial hypothalamic nucleus |
| VTA | ventral tegmental area |

The following device and system abbreviations are used throughout this application:

| | |
|---|---|
| CPS | a clinician programming system |
| DBS | Deep Brain Stimulation |
| HHP | hand held programmer |
| IPG | implantable signal/pulse generator |
| MDS | manufacturing and diagnostic system |
| RF | radio-frequency |
| SCU | system control unit(s) |

The hypothalamus has been demonstrated experimentally in animal studies to exert significant control over feeding behavior. In addition, it is hypothesized that the hypothalamus controls a variety of bodily and cellular functions (e.g., metabolic rate) in order to maintain a set-point for body weight. The hypothalamus is divided into small functional collections of cells known as nuclei; in patients with eating disorders, one or more nuclei in the hypothalamus may demonstrate abnormal behavior.

Some of the neurons in the arcuate nucleus of the hypothalamus secrete a neurotransmitter known as Neuropeptide Y (NPY). These NPY-secreting neurons project to several other hypothalamic nuclei. Increased secretion of NPY leads to abnormally increased appetite for food (hyperphagia), increased body weight, and reduced energy expenditure. In fact, NPY is the most potent central (i.e., acts in the brain/spinal cord) appetite stimulant known. In addition, it is believed that unfavorable metabolic situations, such as diabetes, produce enhanced NPY gene expression and NPY release in the hypothalamus.

NPY also leads to endocrinological disturbances, including increased secretion of adrenocorticotrophic hormone (ACTH) and glucocorticoids, and decreased secretion of luteinizing hormone (LH), follicle-stimulating hormone (FSH), growth hormone (GH), and thyroid stimulating hormone (TSH). Increased levels of glucocorticoids stimulate feeding, favor fat accumulation, and are essential to the development of obesity syndromes in rats. ACTH and glucocorticoid levels have been found to be increased in patients with eating disorders.

Leptin, a protein secreted by adipose (i.e., fat) cells, is believed to inhibit NPY neurons in the arcuate nucleus. In normal subjects, leptin acts via the leptin receptor in the hypothalamus to cause an abnormally decreased appetite for food (hypophagia), increased heat generation (thermogenesis), and loss of body fat. However, mice with an absence of leptin or with a defect in the hypothalamic leptin receptor develop obesity. Serotonin is also believed to inhibit the secretion of NPY.

The paraventricular nucleus of the hypothalamus receives significant input from the NPY-secreting neurons of the arcuate nucleus. Destruction of the region of the paraventricular nucleus leads to hyperphagia, reduced energy expenditure, and obesity in otherwise normal subjects. Excess NPY may also promote these effects.

The ventromedial nucleus of the hypothalamus stimulates thermogenesis and energy expenditure. Destruction of the region of the ventromedial nucleus leads to hyperphagia, reduced energy expenditure, and obesity. For instance, a lesion to the ventromedial nucleus causes an animal to eat voraciously; this area has thus been hypothesized to be "the satiety center." In addition, for centrally administered NPY, the ventromedial nucleus is believed to be a crucial site of NPY-induced feeding.

The lateral hypothalamic area of the tuberal region inhibits thermogenesis. Destruction of the lateral hypothalamus region leads to anorexia and wasting. For instance, a lesion placed in the lateral hypothalamic area abolishes eating and drinking behavior; this area has thus been hypothesized to be "the feeding center".

Additional evidence suggests that pathways through each of these areas of the hypothalamus, particularly noradrenergic pathways destined for more rostral regions, may also exert significant control over appetite.

The nucleus of the solitary tract lies in the brainstem, but it projects to the hypothalamus. It receives gustatory (i.e., sense of taste) and other signals via afferent nerve fibers, as well as through direct contact with systemic circulation (via fenestrated capillaries that allow circulating proteins and other substances to bypass the blood-brain barrier). The nucleus of the solitary tract is involved in controlling energy homeostasis, and destruction in the region of this nucleus leads to increased consumption of food.

The hypothalamic areas that regulate metabolism also receive input from other structures in the brainstem, cerebral cortex, and structures of the limbic system of the brain. Various adrenergic and noradrenergic cell groups in the medulla project to the paraventricular nucleus and the dorsomedial nucleus of the hypothalamus. The arcuate nucleus and the paraventricular nucleus receive serotonergic input from fibers in the raphe nuclei in the brainstem. The ventromedial nucleus and the paraventricular nucleus also receive a cholecystokinin-containing projection relayed from the vagal nuclei via the parabrachial nucleus in the pons (i.e., the pontine taste center).

Ghrelin, a peptide hormone, has been shown to increase food intake in rats under conditions of both fasting and satiety. Furthermore, ghrelin antagonists have been demonstrated to suppress feeding in rats. Ghrelin acts on the arcuate nucleus in the hypothalamus, among other sites, and appears to act as a leptin antagonist.

Agouti-Related Protein (AGRP) is present in increased levels in obese and diabetic mice. It is produced in the hypothalamic arcuate nucleus and can stimulate hyperphagia when over expressed. The type of AGRP produced may vary slightly between individual humans; the variation may be as minor as a difference in one amino acid in the protein. One of these types has been demonstrated to be significantly associated with high body mass index (BMI, a measure of obesity) and type 2 diabetes in Africans. AGRP switches off the melanocortin 4 receptor (MC4-R) and possibly the melanocortin 3 receptor (MC3-R), among others.

Orexin-A and orexin-B are neuropeptides found in the lateral hypothalamus. These neuropeptides and their associated receptors, OX1R and OX2R, have been demonstrated to stimulate the appetite of laboratory rats. Both increase food intake in a dose-related fashion, with orexin-A significantly more effective than orexin-B. Furthermore, when the food intake of the rats was limited, even more of the neuropeptides was produced, as might be expected of a hormone that physiologically regulates appetite.

Additional substances that may act on the hypothalamus to contribute to the development of eating disorders or the symptoms thereof include catecholamines, such as epinephrine and norepinephrine. Various adrenergic and noradrenergic cell groups in the medulla project to the paraventricular nucleus and the dorsomedial nucleus of the hypothalamus.

Additional substances that may act on the hypothalamus to retard or prevent development of eating disorders or the symptoms thereof include corticotropin releasing factor (CRF), bombesin, glucagon-like peptide 1, serotonin, and cholecystokinin. For instance, the arcuate nucleus and the paraventricular nucleus receive serotonergic input from fibers in the raphe nuclei in the brainstem. Serotonin is believed to block the secretion of NPY. The ventromedial nucleus and the paraventricular nucleus of the hypothalamus also receive a cholecystokinin-containing projection relayed from the vagal nuclei via the parabrachial nucleus in the pons (i.e., the pontine taste center).

Additional mediators acting on the central nervous system include dynorphin, melanin-concentrating hormone, melanocyte-stimulating hormone, growth hormone-releasing hormone (GHRH), endocannobinoids, beta-endorphin and galanin. Galanin stimulates feeding behavior whether injected intracerebroventricular (ICV) or into the PVN. Further inhibitors of food intake that act when administered either centrally or peripherally, include dopamine, leptin, and cholecystokinin (CCK).

Low-frequency electrical stimulation (i.e., less than about 100-150 Hz) has been demonstrated to excite neural tissue, leading to increased neural activity. In the brain, and depending on the dimensions, electrical tissue impedance, and other characteristics of the nerve or area to be stimulated, low frequency stimulation may be considered equal to or less than about 100 Hz. Similarly, excitatory neurotransmitters, agonists thereof, and agents that act to increase levels of an excitatory neurotransmitter(s) have been shown to excite neural tissue, leading to increased neural activity. Inhibitory neurotransmitters have been shown to inhibit neural tissue, leading to decreased neural activity; however, antagonists of inhibitory neurotransmitters and agents that act to decrease levels of an inhibitory neurotransmitter(s) tend to excite neural tissue, leading to increased neural activity.

High-frequency electrical stimulation (i.e., greater than about 100-150 Hz) is believed to have an inhibitory effect on neural tissue, leading to decreased neural activity. In the brain, and depending on the dimensions, electrical tissue impedance, and other characteristics of the nerve or area to be stimulated, high frequency stimulation may be considered equal to or greater than about 100 Hz. Similarly, inhibitory neurotransmitters, agonists thereof, and agents that act to increase levels of an inhibitory neurotransmitter(s) have an inhibitory effect on neural tissue, leading to decreased neural activity. Excitatory neurotransmitters have been demonstrated to excite neural tissue, leading to increased neural activity; however, antagonists of excitatory neurotransmitters and agents that act to decrease levels of an excitatory neurotransmitter(s) inhibit neural tissue, leading to decreased neural activity.

Electrical stimulatory SCU are capable of controlled delivery of frequency. Thus, the reaction of the individual to the area stimulated can be assessed and the frequency adjusted to provide either an increased or inhibited response. In one embodiment of the invention, a method is provided for customized assessment of programming of the implanted system, which may be adjusted as therapy continues.

Electrical stimulation has been proposed for treating eating disorders. However, electrical stimulation was applied to the vagus nerve (U.S. Pat. Nos. 5,188,104 and 5,263,480) or to the trigeminal and/or glossopharyngeal nerve (U.S. Pat. No. 5,540,734). Deep Brain Stimulation (DBS) has also been proposed for the treatment of eating disorders. U.S. Pat. No. 5,782,798 to Rise discloses a device for electrically stimulating and/or delivering a drug into the paraventricular nucleus, the ventromedial nucleus, or the lateral hypothalamus. These devices require significant surgical procedures for placement of electrodes, catheters, leads, and/or processing units. These devices may also require an external apparatus that needs to be strapped or otherwise affixed to the skin.

In addition, in the above-noted U.S. Pat. Nos. 5,188,104 and 5,263,480, Wernicke et al., propose manually activating the stimulator or automatically stimulating at what would be a normal mealtime or during normal between-meal times, or the system may sense food in the esophagus or the stomach. For instance, the system may estimate an amount of food consumed by summing the number of swallows over a given period. The system may initiate therapy based on amount of food in the stomach, amount of food swallowed, or a certain time period since swallowing food.

As described above, several hypothalamic nuclei, and other neural tissue within the brain, demonstrate abnormal behavior in patients with eating disorders. Herein, eating disorders (ED) include obesity, morbid obesity, bulimia nervosa, anorexia nervosa (commonly, as herein, simply referred to as anorexia), and other less known eating disorders, such as binge eating disorder (compulsive eating), anorexia athletica (compulsive exercising), body dysmorphic disorder, muscle dysmorphia, night-eating syndrome, nocturnal sleep-related eating disorder, Gourmand syndrome, Prader-Willi syndrome, pica, cyclic vomiting syndrome, and the like.

Figure 1A:
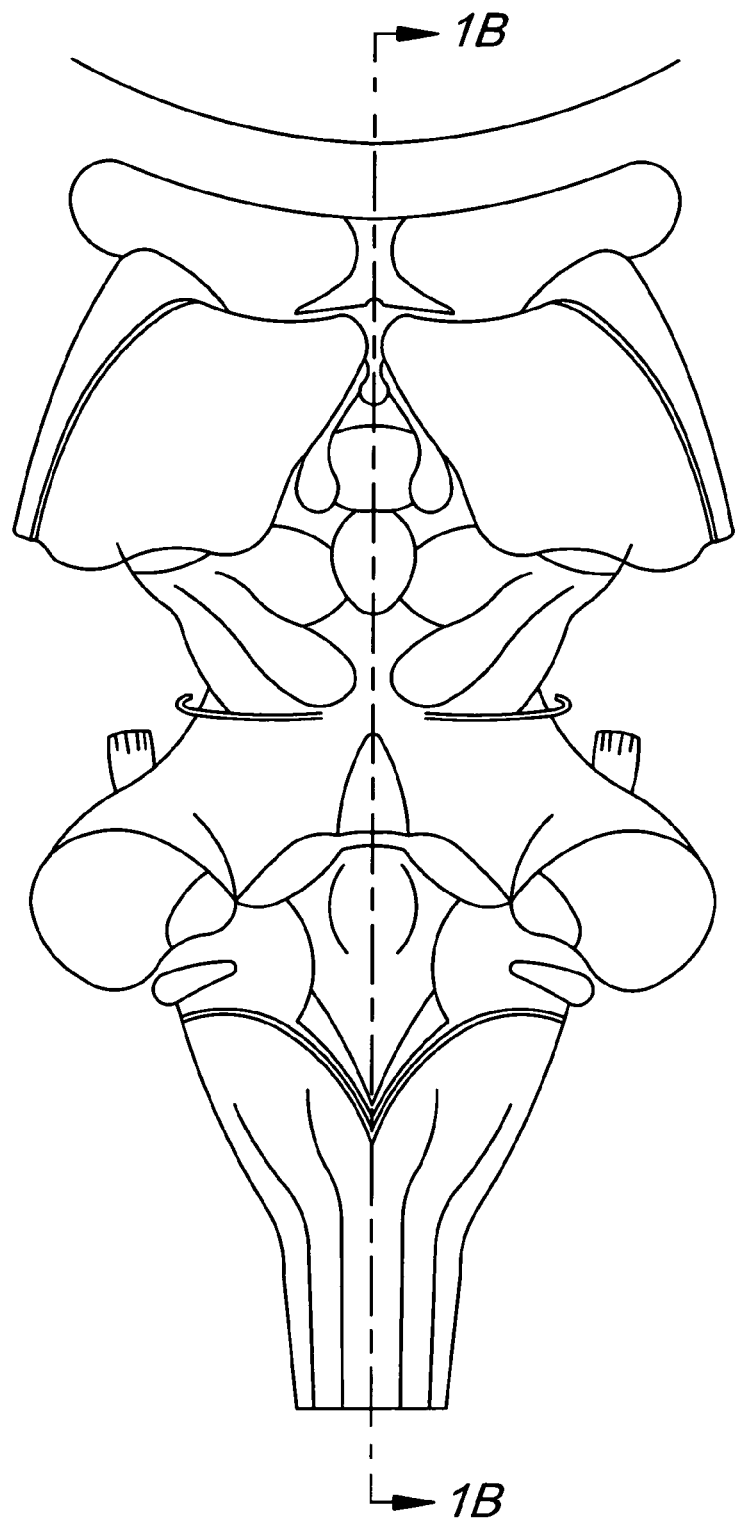
FIG. 1A depicts the dorsal surface of the brain stem.
Figure 1B:
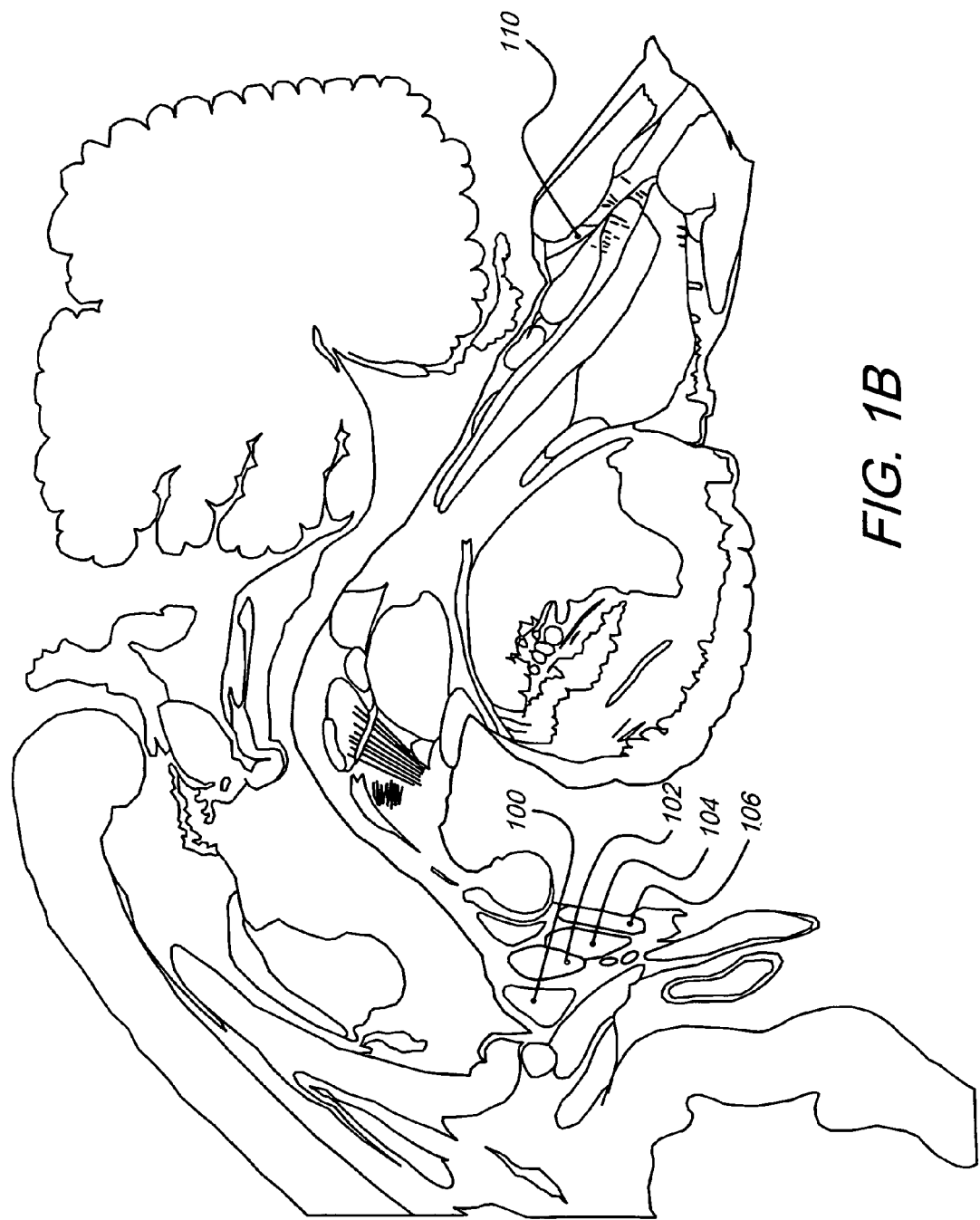
FIG. 1B is a section view through the brain stem depicted in FIG. 1A.
Figure 2A:
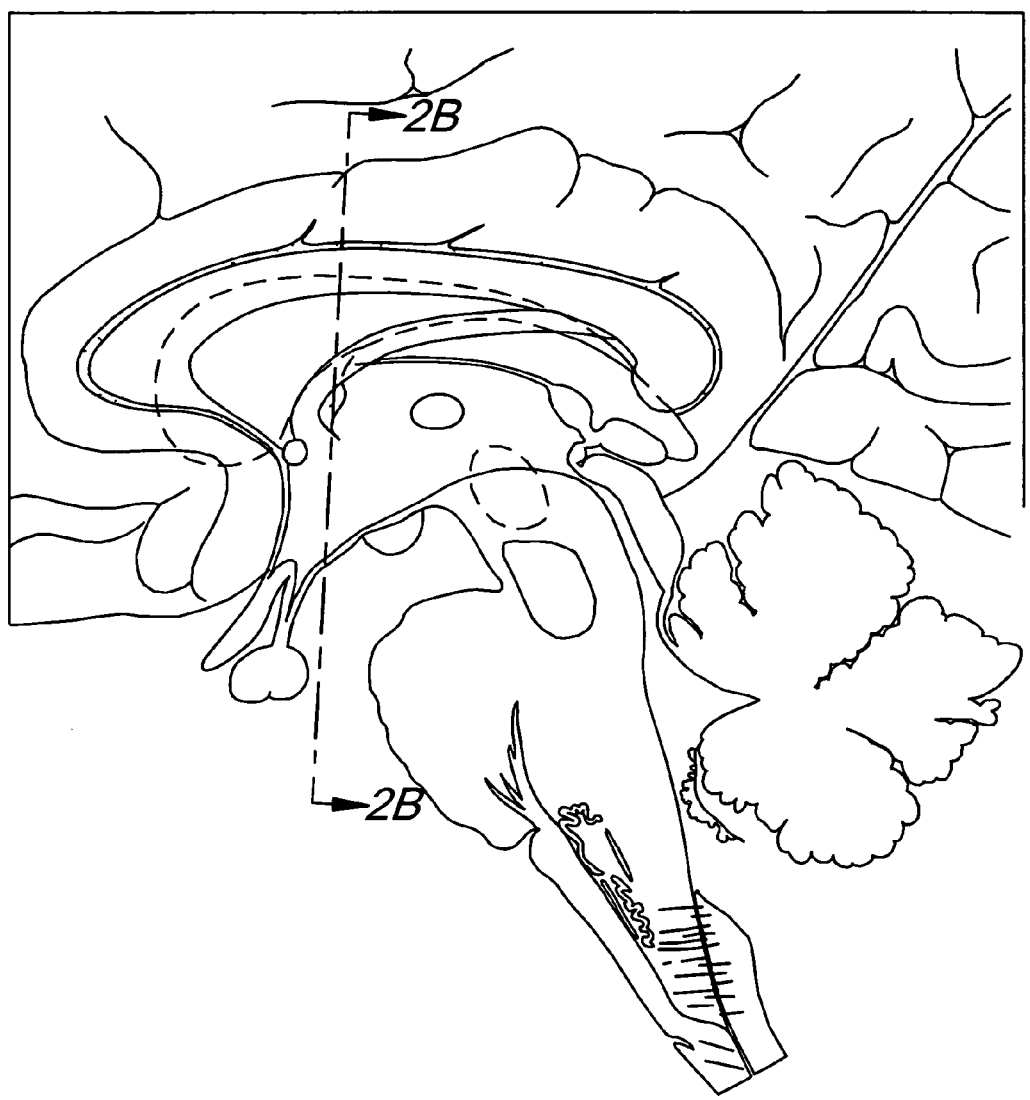
FIG. 2A depicts the medial surface of the brain stem.
Figure 2B:
FIG. 2B is a section view through the brain stem depicted in FIG. 2A.

FIG. 1A depicts the dorsal surface of the brain stem, and FIG. 1B is a section view through the brain stem depicted in FIG. 1A, showing the locations of some of these hypothalamic nuclei: paraventricular nucleus 100, dorsomedial nucleus 102, ventromedial nucleus 104, and arcuate nucleus 106. FIG. 1B also shows the nucleus of the solitary tract 110. FIG. 2A depicts the medial surface of the brain stem, and FIG. 2B is a section view through the brain stem depicted in FIG. 2A, showing the lateral hypothalamic area 112, as well as the paraventricular nucleus 100, dorsomedial nucleus 102, ventromedial nucleus 104, and arcuate nucleus 106.

The present invention provides electrical and/or drug stimulation to at least one or more of the above mentioned areas as a treatment for obesity and/or other eating disorders. Herein, stimulating drugs comprise medications, anesthetic agents, synthetic or natural hormones, neurotransmitters, cytokines and other intracellular and intercellular chemical signals and messengers, and the like. Certain neurotransmitters, hormones, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug. In addition, stimulation of an area herein may include stimulation of cell bodies and axons in the area.

In some alternatives, an implantable signal generator and electrode(s) and/or an implantable pump and catheter(s) are used to deliver electrical stimulation and/or one or more stimulating drugs to specific areas in the brain. One or more electrodes are surgically implanted in the brain to provide electrical stimulation, and/or one or more catheters are implanted in the brain to infuse the stimulating drug(s).

The invention includes at least one system control unit (SCU). It will be recognized that an SCU, also referred to herein as a stimulator, may include an implantable pulse generator (EPG) coupled to a lead of electrodes, a spinal cord stimulator (SCS), a cochlear implant, a deep brain stimulator, a drug pump, a microstimulator, a micro-drug pump or any other type of implantable stimulator configured to deliver electrical and/or drug stimulation. Exemplary IPGs suitable for use as described herein include, but are not necessarily limited to, those disclosed in U.S. Pat. Nos. 6,381,496, 6,553,263; and 6,760,626. Exemplary spinal cord stimulators suitable for use as described herein include, but are not necessarily limited to, those disclosed in U.S. Pat. Nos. 5,501,703; 6,487,446; and 6,516,227. Exemplary cochlear implants suitable for use as described herein include, but are not necessarily limited to, those disclosed in U.S. Pat. Nos. 6,219,580; 6,272,382; and 6,308,101. Exemplary deep brain stimulators suitable for use as described herein include, but are not necessarily limited to, those disclosed in U.S. Pat. Nos. 5,938,688; 6,016,449; and 6,539,263.

Exemplary drug pumps suitable for use as described herein include, but are not necessarily limited to, those disclosed in U.S. Pat. Nos. 4,562,751; 4,678,408; 4,685,903; 5,080,653; 5,097,122; 6,740,072; and 6,770,067. Additional drug pumps may include convective drug delivery system, e.g., systems based upon electroosmosis, vapor pressure pumps, electrolytic pumps, effervescent pumps, piezoelectric pumps and osmotic pumps. Such pumps or controlled drug release devices suitable for use as described herein include, but are not necessarily limited to, those disclosed in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,360,019; 4,487,603; 4,627,850; 4,692,147; 4,725,852; 4,865,845; 5,057,318; 5,059,423; 5,112,614; 5,137,727; 5,234,692; 5,234,693; 5,728,396; 6,368,315 and the like.

Exemplary micro-drug pumps suitable for use as described herein include, but are not necessarily limited to, those disclosed in U.S. Patent Pub. No. 2004/0082908 and U.S. Pat. Nos. 5,234,692; 5,234,693; 5,728,396; 6,368,315; 6,666,845; and 6,620,151. All of these listed patents and publications are incorporated herein by reference in their respective entireties.

In some embodiments, electrical stimulation is provided by one or more system control units (SCUs) that are small, implantable stimulators, referred to herein as microstimulators. Exemplary microstimulators suitable for use as described herein include, but are not necessarily limited to, those disclosed in U.S. Pat. Nos. 5,193,539; 5,193,540; 5,312,439; 6,185,452; 6,164,284; 6,208,894; and 6,051,017. The microstimulators of the present invention may be similar to or of the type referred to as BION® devices (see FIGS. 3A, 3B, and 3C). As shown in FIGS. 3A, 3B, and 3C, microstimulator SCUs 160 may include a narrow, elongated capsule 152 containing electronic circuitry 154 connected to electrodes 172 and 172', which may pass through the walls of the capsule at either end. Alternatively, electrodes 172 and/or 172' may be built into the case and/or arranged on a catheter 180 (FIG. 3B) or at the end of a lead, as described below. As detailed in the referenced patents, electrodes 172 and 172' generally comprise a stimulating electrode (to be placed close to the target tissue) and an indifferent electrode (for completing the circuit). Other configurations of microstimulator SCU 160 are possible, as is evident from the above-referenced patent publications, and as described in more detail herein.

Certain configurations of implantable microstimulator SCU 160 are sufficiently small to permit placement in or adjacent to the structures to be stimulated. For instance, in these configurations, capsule 152 may have a diameter of about 4-5 mm, or only about 3 mm, or even less than about 3 mm. In these configurations, capsule length may be about 25-35 mm, or only about 20-25 mm, or even less than about 20 mm. The shape of the microstimulator may be determined by the structure of the desired target, the surrounding area, and the method of implantation. A thin, elongated cylinder with electrodes at the ends, as shown in FIGS. 3A, 3B, and 3C, is one possible configuration, but other shapes, such as cylinders, disks, spheres, and helical structures, are possible, as are additional electrodes, infusion outlets, leads, and/or catheters.

Microstimulator SCU 160, when certain configurations are used, may be implanted with a surgical insertion tool such as the tool specially designed for the purpose, or may be injected (e.g., via a hypodermic needle). Alternatively, microstimulator SCU 160 may be implanted via conventional surgical methods, or may be inserted using other endoscopic or laparoscopic techniques. A more complicated surgical procedure may be required for fixing the microstimulator in place.

The external surfaces of microstimulator SCU 160 may advantageously be composed of biocompatible materials. Capsule 152 may be made of, for instance, glass or ceramic to provide a hermetic package that will exclude water vapor but permit passage of electromagnetic fields used to transmit data and/or power. Electrodes 172 and 172' may be made of a conducting ceramic, conducting polymer, and/or a noble or refractory metal, such as gold, silver, platinum, iridium, tantalum, titanium, titanium nitride, niobium or their alloys that, e.g., minimize corrosion, electrolysis, and damage the surrounding tissues.

In certain embodiments of the instant invention, microstimulator SCU 160 comprises two, leadless electrodes. However, either or both electrodes 172 and 172' may alternatively be located at the ends of short, flexible leads as described in U.S. patent application Ser. No. 09/624,130, filed Jul. 24, 2000, which is incorporated herein by reference in its entirety. The use of such leads permits, among other things, electrical stimulation to be directed more locally to targeted tissue(s) a short distance from the surgical fixation of the bulk of microstimulator SCU 160, while allowing most elements of the microstimulator to be located in a more surgically convenient site. This minimizes the distance traversed and the surgical planes crossed by the device and any lead(s). In most uses of this invention, the leads may be no longer than about 150 mm.

As mentioned earlier, stimulation is provided in accordance with the teachings of the present invention by electrical stimulation and/or one or more stimulating drugs. The invention includes one or more system control units (SCUs). In the case of electrical stimulation only, SCUs include a microstimulator and/or an implantable pulse/signal generator (IPG), or the like. In the case of drug infusion only, an SCU comprises an implantable pump or the like. In cases requiring both electrical stimulation and drug infusion, more than one SCU may be used. Alternatively, when needed and/or desired, an SCU provides both electrical stimulation and one or more stimulating drugs.

As depicted in FIG. 4, some embodiments of SCU 160 may be (but are not necessarily) implanted beneath the scalp, such as in a surgically-created shallow depression or opening in the skull 140, for instance, in parietal bone 141, temporal bone 142, or frontal bone 143. In several embodiments, SCU 160 conforms to the profile of surrounding tissue(s) and/or bone (s), and is small and compact. This may minimize upward pressure applied to the skin or scalp, which pressure may result in skin erosion or infection. In various embodiments, SCU 160 has a diameter of about 75 mm, or only about 65 mm, or even less than about 55 mm. In these configurations, SCU thickness may be approximately 10-12 mm, or even less than about 10 mm.

As seen in the embodiments depicted in FIG. 5, one or more electrode leads 170 and/or catheters 180 attached to SCU 160 run subcutaneously, for instance, in a surgically-created shallow groove(s) in the skull, to an opening(s) in the skull, and pass through the opening(s) into or onto the brain parenchyma and surrounding tissue. Recessed placement of the SCU and the lead(s) and/or catheter(s) may decrease the likelihood of erosion of overlying skin, and may minimize any cosmetic impact.

In embodiments such as in FIG. 5, electrode(s) 172 are carried on lead 170 having a proximal end coupled to SCU 160. The lead contains wires electrically connecting electrodes 172 to SCU 160. SCU 160 contains electrical components 154 that produce electrical stimulation pulses that travel through the wires of lead 170 and are delivered to electrodes 172, and thus to the tissue surrounding electrodes 172. To protect the electrical components inside SCU 160, some or all of the case of the SCU may be hermetically sealed. For additional protection against, e.g., impact, the case may be made of metal (e.g. titanium) or ceramic, which materials are also, advantageously, biocompatible. In addition, SCU 160 may be configured to be Magnetic Resonance Imaging (MRI) compatible.

In some alternatives, the electrical stimulation may be provided as described in International Patent Application Serial Number PCT/US01/04417 (the '417 application), filed Feb. 12, 2001, which application is incorporated herein by reference in its entirety. As such, the electrical stimulation of the present invention may be as provided in this PCT application, which is directed to a "Deep Brain Stimulation System for the Treatment of Parkinson's Disease or Other Disorders."

In the case of treatment alternatively or additionally constituting drug infusion, SCU 160 may contain at least one pump 162 for storing and dispensing one or more drugs through infusion outlet(s) 182 and/or catheter(s) 180 into a predetermined site(s) in the brain tissue. When a catheter is used, it includes at least one infusion outlet 182, usually positioned at least at a distal end, while a proximal end of the catheter is connected to SCU 160.

According to some embodiments of the invention, such as described in the previously referenced '417 application and as depicted in FIG. 5, at least one lead 170 is attached to SCU 160, via a suitable connector 168, if necessary. Each lead includes at least two electrodes 172, and may include as many as sixteen or more electrodes 172. Additional leads 170' and/or catheter(s) 180' may be attached to SCU 160. Hence, FIG. 5 shows (in phantom lines) a second catheter 180', and a second lead 170', having electrodes 172' thereon, also attached to SCU 160. Similarly, the SCUs 160 of FIGS. 3A, 3B, and 3C have outlets 182, 182' for infusing a stimulating drug(s) and electrodes 172, 172' for applying electrical stimulation.

Lead(s) 170 of certain embodiments of the present invention may be less than about 5 mm in diameter, or even less than about 1.5 mm in diameter. Electrodes 172, 172' on leads 170, 170' may be arranged as an array, for instance, as two or more collinear electrodes, or even as four or more collinear electrodes, or they may not be collinear. A tip electrode may also be supplied at the distal end of one or more leads. In some embodiments, SCU 160 is programmable to produce either monopolar electrical stimulation, e.g., using the SCU case as an indifferent electrode, or bipolar electrical stimulation, e.g., using one of the electrodes of the electrode array as an indifferent electrode. Some embodiments of SCU 160 have at least four channels and drive up to sixteen electrodes or more.

SCU 160 (which herein refers to IPGs, implantable pumps, IPG/pump combinations, microstimulators for drug and/or electrical stimulation, other alternative devices described herein, and the like) contains, when necessary and/or desired, electronic circuitry 154 for receiving data and/or power from outside the body by inductive, radio frequency (RF), or other electromagnetic coupling. In some embodiments, electronic circuitry 154 includes an inductive coil for receiving and transmitting RF data and/or power, an integrated circuit (IC) chip for decoding and storing stimulation parameters and generating stimulation pulses (either intermittent or continuous), and additional discrete electronic components required to complete the electronic circuit functions, e.g. capacitor(s), resistor(s), coil(s), and the like.

SCU 160 also includes, when necessary and/or desired, a programmable memory 164 for storing a set(s) of data, stimulation, and control parameters. Among other things, memory 164 may allow electrical and/or drug stimulation to be adjusted to settings that are safe and efficacious with minimal discomfort for each individual. Specific parameters may provide therapy for various eating disorders and levels of obesity. For instance, some patients may respond favorably to intermittent stimulation, while others may require continuous treatment for relief. In some embodiments, electrical and drug stimulation parameters are controlled independently. In various embodiments, they are coupled, e.g., electrical stimulation is programmed to occur only during drug infusion.

In addition, parameters may be chosen to target specific neural populations and to exclude others, or to increase neural activity in specific neural populations and to decrease neural activity in others. For example, relatively low frequency neurostimulation (i.e., less than about 100 Hz) typically has an excitatory effect on surrounding neural tissue in the brain, leading to increased neural activity, whereas relatively high frequency neurostimulation (i.e., greater than about 100-150 Hz) may have an inhibitory effect, leading to decreased neural activity. Similarly, excitatory neurotransmitters (e.g., acetylcholine), agonists thereof, and agents that increase levels of an excitatory neurotransmitter(s) (e.g., edrophonium) generally have an excitatory effect on neural tissue, while inhibitory neurotransmitters (e.g., gamma-aminobutyric acid, a.k.a. GABA), agonists thereof, and agents that act to increase levels of an inhibitory neurotransmitter(s) generally have an inhibitory effect. However, antagonists of inhibitory neurotransmitters (e.g., bicuculline) and agents that act to decrease levels of an inhibitory neurotransmitter(s) have been demonstrated to excite neural tissue, leading to increased neural activity. Similarly, excitatory neurotransmitter antagonists (e.g. atropine) and agents that decrease levels of excitatory neurotransmitters may inhibit neural activity.

Some embodiments of SCU 160 also include a power source and/or power storage device 166. Possible power options for a stimulation device of the present invention, described in more detail below, include but are not limited to an external power source coupled to the stimulation device, e.g., via an RF link, a self-contained power source utilizing any means of generation or storage of energy (e.g., a primary battery, a rechargeable battery such as a lithium ion battery, an electrolytic capacitor, or a super- or ultra-capacitor), and if the self-contained power source is replenishable or rechargeable, means of replenishing or recharging the power source (e.g., an RF link).

In embodiments such as shown in FIG. 5, SCU 160 includes a rechargeable battery as a power source/storage device 166. The battery is recharged, as required, from an external battery charging system (EBCS) 192, typically through an inductive link 194. In these embodiments, and as explained more fully in the earlier referenced '417 PCT application, SCU 160 includes a processor and other electronic circuitry 154 that allow it to generate stimulation pulses that are applied to a patient 208 through electrodes 172 and/or outlet(s) 182 in accordance with a program and stimulation parameters stored in programmable memory 164. Stimulation pulses of drugs include various types and/or rates of infusion, such as intermittent infusion, infusion at a constant rate, and bolus infusion.

According to certain embodiments of the invention, an SCU operates independently. According to various embodiments of the invention, an SCU operates in a coordinated manner with other SCU(s), other implanted device(s), or other device(s) external to the patient's body. For instance, an SCU may control or operate under the control of another implanted SCU(s), other implanted device(s), or other device (s) external to the patient's body. An SCU may communicate with other implanted SCUs, other implanted devices, and/or devices external to a patient's body via, e.g., an RF link, an ultrasonic link, or an optical link. Specifically, an SCU may communicate with an external remote control (e.g., patient and/or physician programmer) that is capable of sending commands and/or data to an SCU and that may also be capable of receiving commands and/or data from an SCU.

For example, some embodiments of SCU 160 of the present invention may be activated and deactivated, programmed and tested through a hand held programmer (HHP) 200 (which may also be referred to as a patient programmer and may be, but is not necessarily, hand held), a clinician programming system (CPS) 202 (which may also be hand held), and/or a manufacturing and diagnostic system (MDS) 204 (which may also be hand held). HHP 200 may be coupled to SCU 160 via an RF link 195. Similarly, MDS 204 may be coupled to SCU 160 via another RF link 196. In a like manner, CPS 202 may be coupled to HHP 200 via an infra-red link 197; and MDS 204 may be coupled to HHP 200 via another infra-red link 198. Other types of telecommunicative links, other than RF or infra-red may also be used for this purpose. Through these links, CPS 202, for example, may be coupled through HHP 200 to SCU 160 for programming or diagnostic purposes. MDS 204 may also be coupled to SCU 160, either directly through the RF link 196, or indirectly through IR link 198, HHP 200, and RF link 195.

In certain embodiments, using for example, a BION microstimulator(s) as described in the above referenced patents, and as illustrated in FIG. 6, the patient 208 switches SCU 160 on and off by use of controller 210, which may be handheld. Controller 210 operates to control SCU 160 by any of various means, including sensing the proximity of a permanent magnet located in controller 210, sensing RF transmissions from controller 210, or the like.

External components for programming and providing power to various embodiments of SCU 160 are also illustrated in FIG. 6. When communication with such an SCU 160 is desired, patient 208 is positioned on or near external appliance 220, which appliance contains one or more inductive coils 222 or other means of communication (e.g., RF transmitter and receiver). External appliance 220 is connected to or is a part of external electronic circuitry appliance 230 which may receive power 232 from a conventional power source. External appliance 230 contains manual input means 238, e.g., a keypad, whereby the patient 208 or a caregiver 242 may request changes in electrical and/or drug stimulation parameters produced during the normal operation of SCU 160. In these embodiments, manual input means 238 includes various electromechanical switches and/or visual display devices that provide the patient and/or caregiver with information about the status and prior programming of SCU 160.

Alternatively or additionally, external electronic appliance 230 is provided with an electronic interface means 246 for interacting with other computing means 248, such as by a serial interface cable or infrared link to a personal computer or to a telephone modem or the like. Such interface means 246 may permit a clinician to monitor the status of the implant and prescribe new stimulation parameters from a remote location.

The external appliance(s) may be embedded in a cushion, pillow, or hat. Other possibilities exist, including a head band or other structure that may be affixed to the patient's body or clothing.

In order to help determine the strength and/or duration of electrical stimulation and/or the amount and/or type(s) of stimulating drug(s) required to produce the desired effect, in some embodiments, a patient's response to and/or need for treatment is sensed. For example, electrical activity of the brain (e.g., EEG), nerve activity (e.g., ENG), muscle activity (e.g., EMG), or other activity may be sensed. Additionally or alternatively, one or more neurotransmitter levels and/or their associated breakdown product levels, hormone levels, or other substances, such as ketone levels, cytokines, glucose, electrolytes, enzymes, medication, and/or other drug levels, levels of one or more catecholamines, and/or any other bloodborne substance may be sensed. For example, levels of one or more neurotransmitters, such as Neuropeptide Y (NPY) and/or serotonin, may be sensed. Levels of one or more hormones or other substances, such as adrenocorticotrophic hormone (ACTH), luteinizing hormone (LH), follicle-stimulating hormone (FSH), growth hormone (GH), thyroid stimulating hormone (TSH), leptin, ghrelin, agouti-related protein (AGRP), orexin-A, orexin-B, cholecystokinin (CCK), glucagon, glucocorticoids, and the like may be sensed.

For example, when electrodes of SCU 160 are implanted adjacent to the arcuate nucleus 106 of the hypothalamus, a stimulating electrode of SCU 160, or other sensing means, may be used to sense changes in NPY level resulting from the electrical and/or drug stimulation applied to the arcuate nucleus 106. (As used herein, "adjacent" or "near" means as close as reasonably possible to targeted tissue, including touching or even being positioned within the tissue, but in general, may be as far as about 150 mm from the target tissue.)

Alternatively, an "SCU" that is dedicated to sensory processes communicates with an SCU that provides the stimulation pulses. The implant circuitry 154 may, if necessary, amplify and transmit these sensed signals, which may be digital or analog. Other methods of determining the required electrical and/or drug stimulation include measuring impedance, acidity/alkalinity (via a pH sensor), body mass, and other methods mentioned herein, and others that will be evident to those of skill in the art upon review of the present disclosure. The sensed information may be used to control stimulation parameters in a closed-loop manner.

For instance, in several embodiments of the present invention, a first and second "SCU" are provided. The second "SCU" periodically (e.g. once per minute) records NPY level (or the level of some other substance, or an amount of electrical activity, etc.), which it transmits to the first SCU. The first SCU uses the sensed information to adjust electrical and/or drug stimulation parameters according to an algorithm programmed, e.g., by a physician. For example, the amplitude of electrical stimulation may be increased in response to increased NPY levels. In some alternatives, one SCU performs both the sensing and stimulating functions, as discussed in more detail presently.

While an SCU 160 may also incorporate means of sensing symptoms or other prognostic or diagnostic indicators of eating disorders, e.g., via levels of a neurotransmitter or hormone, it may alternatively or additionally be desirable to use a separate or specialized implantable device to record and telemeter physiological conditions/responses in order to adjust electrical stimulation and/or drug infusion parameters. This information may be transmitted to an external device, such as external appliance 220, or may be transmitted directly to implanted SCU(s) 160. However, in some cases, it may not be necessary or desired to include a sensing function or device, in which case stimulation parameters are determined and refined, for instance, by patient feedback, or the like.

Thus, it is seen that in accordance with the present invention, one or more external appliances may be provided to interact with SCU 160, and may be used to accomplish, potentially among other things, one or more of the following functions:

Function 1: If necessary, transmit electrical power from the external electronic appliance 230 via appliance 220 to SCU 160 in order to power the device and/or recharge the power source/storage device 166. External electronic appliance 230 may include an automatic algorithm that adjusts electrical and/or drug stimulation parameters automatically whenever the SCU(s) 160 is/are recharged.

Function 2: Transmit data from the external appliance 230 via the external appliance 220 to SCU 160 in order to change the parameters of electrical and/or drug stimulation produced by SCU 160.

Function 3: Transmit sensed data indicating a need for treatment or in response to stimulation from SCU 160 (e.g., electrical activity of the brain, nerve activity, muscle activity, neurotransmitter levels, levels of neurotransmitter breakdown products, impedance, acidity/alkalinity, body mass, medication levels, hormone levels, or other activity) to external appliance 230 via external appliance 220.

Function 4: Transmit data indicating state of the SCU 160 (e.g., battery level, drug level, stimulation parameters, etc.) to external appliance 230 via external appliance 220.

By way of example, a treatment modality for morbid obesity may be carried out according to the following sequence of procedures:

1. An SCU 160 is implanted so that its electrodes 172 and/or infusion outlet 182 are located in or near the arcuate nucleus 106 of the hypothalamus. If necessary or desired, electrodes 172' and/or infusion outlet(s) 182' may additionally or alternatively be located in or adjacent to neural tissue with receptors for NPY.

2. Using Function 2 described above (i.e., transmitting data) of external electronic appliance 230 and external appliance 220, SCU 160 is commanded to produce a series of electrical stimulation pulses, possibly with gradually increasing amplitude, and possibly while infusing gradually increasing amounts of an NPY antagonist, e.g., NGD 95-1, or a hormone, such as leptin.

3. After each stimulation pulse, or at some other predefined interval, any change in NPY level resulting from the electrical and/or drug stimulation is sensed, for instance, by one or more electrodes 172 and/or 172'. These responses are converted to data and telemetered out to external electronic appliance 230 via Function 3.

4. From the response data received at external appliance 230 from SCU 160, the stimulus threshold for obtaining a response is determined and is used by a clinician 242 acting directly 238 or by other computing means 248 to transmit the desired electrical and/or drug stimulation parameters to SCU 160 in accordance with Function 2.

5. When patient 208 desires to invoke electrical stimulation and/or drug infusion, patient 208 employs controller 210 to set SCU 160 in a state where it delivers a prescribed stimulation pattern from a predetermined range of allowable stimulation patterns.

6. To cease electrical and/or drug stimulation, patient 208 employs controller 210 to turn off SCU 160.

7. Periodically, the patient or caregiver recharges the power source/storage device 166 of SCU 160, if necessary, in accordance with Function 1 described above (i.e., transmit electrical power).

For the treatment of any of the various types and levels of severity of eating disorders, it may be desirable to modify or adjust the algorithmic functions performed by the implanted and/or external components, as well as the surgical approaches, in ways that would be obvious to skilled practitioners of these arts. For example, in some situations, it may be desirable to employ more than one SCU 160, each of which could be separately controlled by means of a digital address. Multiple channels and/or multiple patterns of electrical and/or drug stimulation might thereby be programmed by the clinician and controlled by the patient in order to deal with complex or multiple symptoms or dysfunctions.

In some embodiments discussed earlier, SCU 160, or a group of two or more SCUs, is controlled via closed-loop operation. A need for and/or response to stimulation is sensed via SCU 160, or by an additional SCU (which may or may not be dedicated to the sensing function), or by another implanted or external device. Sensed conditions may be one or more of regional cerebral blood flow (rCBF), body mass, impedance, acidity/alkalinity (via a pH sensor), electrical activity of the brain (e.g., EEG), nerve activity (e.g., ENG), muscle activity (e.g., EMG), or other activity. Additionally or alternatively, neurotransmitter levels and/or their associated breakdown product levels, hormone levels, or other substances, such as ketone levels, cytokines, glucose, electrolytes, enzymes, medication, and/or other drug levels, levels of one or more catecholamines, and/or any other bloodborne substance may be sensed. For example, levels of one or more neurotransmitters, such as Neuropeptide Y (NPY) and/or serotonin, may be sensed. Levels of one or more hormones or other substances, such as adrenocorticotrophic hormone (ACTH), luteinizing hormone (LH), follicle-stimulating hormone (FSH), growth hormone (GH), thyroid stimulating hormone (TSH), leptin, ghrelin, agouti-related protein (AGRP), orexin-A, orexin-B, cholecystokinin (CCK), glucagon, glucocorticoids, and the like may be sensed.

If necessary, the sensed information is transmitted to SCU 160. In some embodiments, the parameters used by SCU 160 are automatically adjusted based on the sensed information. Thus, the electrical and/or drug stimulation parameters are adjusted in a closed-loop manner to provide stimulation tailored to the need for and/or response to the electrical and/or drug stimulation.

For instance, as shown in the example of FIG. 7, a first SCU 160, implanted beneath the skin of the patient 208, provides a first medication or substance; a second SCU 160' provides a second medication or substance; and a third SCU 160" provides electrical stimulation via electrodes 172 and 172'. As mentioned earlier, the implanted devices may operate independently or may operate in a coordinated manner with other similar implanted devices, other implanted devices, or other devices external to the patient's body, as shown by the control lines 262, 263 and 264 in FIG. 7. That is, in accordance with certain embodiments of the invention, the external controller 250 controls the operation of each of the implanted devices 160, 160' and 160". According to various embodiments of the invention, an implanted device, e.g. SCU 160, may control or operate under the control of another implanted device(s), e.g. SCU 160' and/or SCU 160". That is, a device made in accordance with the invention may communicate with other implanted stimulators, other implanted devices, and/or devices external to a patient's body, e.g., via an RF link, an ultrasonic link, an optical link, or the like. Specifically, as illustrated in FIG. 7, SCU 160, 160', and/or 160", made in accordance with the invention, may communicate with an external remote control (e.g., patient and/or physician programmer 250) that is capable of sending commands and/or data to implanted devices and that may also be capable of receiving commands and/or data from implanted devices.

A drug infusion stimulator made in accordance with the invention may incorporate communication means for communicating with one or more external or site-specific drug delivery devices, and, further, may have the control flexibility to synchronize and control the duration of drug delivery. The associated drug delivery device typically provides a feedback signal that lets the control device know it has received and understood commands. The communication signal between the implanted stimulator and the drug delivery device may be encoded to prevent the accidental or inadvertent delivery of drugs by other signals.

An SCU made in accordance with the invention thus incorporates, in some embodiments, first sensing means 268 for sensing therapeutic effects, clinical variables, or other indicators of the state of the patient, such as body mass, impedance, pH, EEG, ENG, EMG, or the like. The stimulator additionally or alternatively incorporates second means 269 for sensing neurotransmitter levels and/or their associated breakdown product levels, medication levels and/or other drug levels, hormone, glucose, ketone, electrolytes, enzyme, and/or cytokine levels and/or changes in these or other substances in the blood plasma or local interstitial fluid. The stimulator additionally or alternatively incorporates third means 270 for sensing electrical current levels and/or waveforms supplied by another source of electrical energy. Sensed information may be used to control infusion and/or electrical parameters in a closed loop manner, as shown by control lines 266, 267, and 265. Thus, the sensing means may be incorporated into a device that also includes electrical and/or drug stimulation, or the sensing means (that may or may not have stimulating means) may communicate the sensed information to another device(s) with stimulating means.

According to some embodiments of the invention, the electrical and/or drug stimulation increases excitement of one or more of those areas of the brain that exhibit chronic decreased activity in patients with eating disorders relative to control subjects, thereby treating or preventing eating disorders and the symptoms and pathological consequences thereof. Such excitatory stimulation is likely to be produced by low-frequency electrical stimulation (e.g., less than about 100-150 Hz, in some instances less than 100 Hz), an excitatory neurotransmitter agonist(s) (e.g., acetylcholine), a medication that increases the level of an excitatory neurotransmitter (e.g., edrophonium), an excitatory hormone agonists(s), an inhibitory neurotransmitter antagonist(s) (e.g., bicuculline), an inhibitory hormone antagonist(s), corticotropin releasing factor (CRF) and/or its agonists, bombesin and/or its agonists, glucagon-like peptide 1 and/or its agonists, serotonin and/or its agonists, leptin and/or its agonists, ghrelin antagonists, AGRP antagonists, MC4-R agonists, MC3-R agonists, orexin-A antagonists, orexin-B antagonists, OX1R antagonists, OX2R antagonists, cholecystokinin and/or its agonists, and/or the like. For example, for patients suffering from obesity and/or the like, this excitatory stimulation may be applied to, among other places, one or more of the paraventricular nucleus 100, the ventromedial nucleus 104, and the nucleus of the solitary tract 110. As another example, for patients suffering from anorexia and/or the like, this excitatory stimulation may be applied to, among other places, one or both of the arcuate nucleus 106 and the lateral hypothalamic area 112.

According to other embodiments of the invention, the electrical and/or drug stimulation decreases excitement of one or more of those areas of the brain that exhibit chronic increased activity in patients with eating disorders relative to control subjects, thereby treating or preventing eating disorders. Such inhibitory stimulation is likely to be produced by high-frequency electrical stimulation (e.g., greater than about 100-150 Hz, in some instances greater than 100 Hz), an inhibitory neurotransmitter agonist(s) (e.g., GABA), a medication that increases the level of an inhibitory neurotransmitter, an inhibitory hormone agonist(s), an excitatory neurotransmitter antagonist(s) (e.g., atropine), an excitatory hormone antagonist(s), and/or the like. For example, for patients suffering from obesity and/or the like, this inhibitory stimulation may also/instead be applied to, among other places, one or both of the arcuate nucleus 106 and the lateral hypothalamic area 112. As another example, for patients suffering from anorexia or the like, this inhibitory stimulation may be applied to, among other places, one or more of the paraventricular nucleus 100, the ventromedial nucleus 104, and the nucleus of the solitary tract 110.

In most embodiments herein, excitatory stimulation may be produced by (but is not limited to) one or more of the following: low-frequency electrical stimulation (e.g., less than about 100-150 Hz), an excitatory neurotransmitter agonist(s) (e.g., acetylcholine), a medication that increases the level of an excitatory neurotransmitter (e.g., edrophonium), an excitatory hormone agonists(s), an inhibitory neurotransmitter antagonist(s) (e.g., bicuculline), an inhibitory hormone antagonist(s), corticotropin releasing factor (CRF) and/or its agonists, bombesin and/or its agonists, glucagon-like peptide 1 and/or its agonists, serotonin and/or its agonists, leptin and/or its agonists, ghrelin antagonists, AGRP antagonists, MC4-R agonists, MC3-R agonists, orexin-A antagonists, orexin-B antagonists, OX1R antagonists, OX2R antagonists, cholecystokinin and/or its agonists, and/or the like. In most embodiments herein, inhibitory stimulation may be produced by (but is not limited to) one or more of the following: high-frequency electrical stimulation (e.g., greater than about 100-150 Hz), an inhibitory neurotransmitter agonist(s) (e.g., GABA, baclofen, muscimol), a medication that increases the level of an inhibitory neurotransmitter, an inhibitory hormone agonist(s), an excitatory neurotransmitter antagonist(s) (e.g., atropine), an excitatory hormone antagonist(s), and/or the like.

According to some embodiments of the invention, the stimulation inhibits the secretion of NPY by the NPY-secreting cells of the arcuate nucleus 106 of the hypothalamus for patients with obesity and/or the like. In addition to the inhibitory stimulation described earlier, insulin, leptin, CRF, serotonin, and/or the like may also/instead be used.

For patients with anorexia and/or the like, certain embodiments of the invention provide stimulation to activate the secretion of NPY by the NPY-secreting cells of the arcuate nucleus 106 of the hypothalamus. Such excitatory stimulation is likely to be produced as described earlier.

According to various embodiments of the invention, for patients with obesity and/or the like, the stimulation inhibits the effects of NPY on the paraventricular nucleus 100, the dorsomedial nucleus 102, the ventromedial nucleus 104, and/or any other neural tissue with receptors for NPY. Such inhibitory action is likely to be produced by high-frequency electrical stimulation, an antagonist(s) of NPY (e.g., PYX-1, BIBP 3226, 1229 U 91, and/or NGD 95-1), and/or the like applied to one or more of the paraventricular nucleus 100, the dorsomedial nucleus 102, the ventromedial nucleus 104, and the arcuate nucleus 106.

In several embodiments of the invention, for patients with anorexia and/or the like, the stimulation produces or enhances the effects of NPY on the paraventricular nucleus 100, the dorsomedial nucleus 102, the ventromedial nucleus 104, and/or any other neural tissue with receptors for NPY. Such excitatory action may be produced by low-frequency electrical stimulation, an agonist(s) of NPY (e.g., a modified version of the NPY peptide), NPY itself, and/or the like applied to these areas.

According to various embodiments of the invention, the stimulation inhibits the production of AGRP by the AGRP-producing cells of the arcuate nucleus 106 for patients with obesity and/or the like. In addition to the inhibitory stimulation described earlier, insulin and/or the like may also/instead be used.

For patients with anorexia and/or the like, some embodiments of the invention provide stimulation to activate and/or promote the production of AGRP by the AGRP-producing cells of the arcuate nucleus 106. Such excitatory stimulation is likely to be produced as described earlier.

According to certain embodiments of the invention, for patients with obesity and/or the like, the stimulation inhibits the effects of AGRP on the paraventricular nucleus 100, the dorsomedial nucleus 102, the arcuate nucleus 106, and/or any other neural tissue with receptors for AGRP. Inhibitory stimulation to these areas is likely to be produced as described earlier.

For patients with anorexia and/or the like, several embodiments of the invention provide stimulation to activate and/or promote the effects of AGRP on the paraventricular nucleus 100, the dorsomedial nucleus 102, the arcuate nucleus 106, and/or any other neural tissue with receptors for AGRP. Excitatory action in these areas may be produced by AGRP itself, an agonist(s) of AGRP, and/or as described earlier.

According to some embodiments of the invention, the stimulation acts as an agonist of MC4-R and/or MC3-R in the paraventricular nucleus 100, dorsomedial nucleus 102, and/or arcuate nucleus 106 for patients with obesity and/or the like. Such excitatory stimulation is likely to be produced as described earlier.

For patients with anorexia and/or the like, certain embodiments of the invention provide stimulation to act as an antagonist of MC4-R and/or MC3-R in the paraventricular nucleus 100, the dorsomedial nucleus 102, and/or the arcuate nucleus 106. Such inhibitory stimulation is likely to be produced as described earlier.

According to various embodiments of the invention, for patients with obesity and/or the like, the stimulation inhibits the production of orexins by the lateral hypothalamus 112, and/or inhibits the action of orexins, for instance by acting as an antagonist(s) of the orexin-A receptor (OX1R) and/or orexin-B receptor (OX2R), in the paraventricular nucleus 100 and/or ventromedial nucleus 104. Such inhibitory stimulation is likely to be produced as described earlier.

For patients with anorexia and/or the like, several embodiments of the invention provide stimulation to promote or enhance the production of orexins by the lateral hypothalamus, and/or promotes or enhances the action of orexins, for instance by acting as an agonist of OX1R and/or OX2R, in the paraventricular nucleus 100 and/or ventromedial nucleus 104. Such excitatory stimulation is likely to be produced as described earlier.

According to some embodiments of the invention, for patients with obesity and/or the like, the stimulation inhibits the effects of one or more catecholamines on the paraventricular nucleus 100, the dorsomedial nucleus 102, and/or any other neural tissue with receptors for catecholamines. Such inhibitory action is likely to be produced by high-frequency electrical stimulation, an antagonist(s) of the catecholamine(s) (e.g., prazosin, metoprolol, and/or carvedilol), and/or the like applied to at least one of the paraventricular nucleus 100 and the dorsomedial nucleus 102.

For patients with anorexia and/or the like, certain embodiments of the invention produce or enhance the effects of one or more catecholamines on the paraventricular nucleus 100, the dorsomedial nucleus 102, and/or other neural tissue with receptors for catecholamines. Such excitatory action is likely produced by low-frequency electrical stimulation, an agonist(s) of the catecholamine(s) (e.g., dextroamphetamine and/or sibutramine), one or more of the catecholamines themselves, and/or the like applied to at least one of the paraventricular nucleus 100 and the dorsomedial nucleus 102.

According to various embodiments of the invention, for patients with obesity and/or the like, the stimulation increases secretion of corticotropin-releasing factor (CRF) by the arcuate nucleus 106. Such excitatory stimulation is likely to be produced as described earlier.

For patients with anorexia and/or the like, several embodiments of the invention decrease secretion of CRF by the arcuate nucleus 106. Such inhibitory stimulation is likely to be produced as described earlier.

According to some embodiments of the invention, for patients with obesity and/or the like, the stimulation increases secretion of gonadotropin-releasing hormone (GnRH), luteinizing hormone releasing hormone (LHRH), and/or thyrotropin releasing hormone (TRH) by the arcuate nucleus 106 of the hypothalamus. Such excitatory stimulation is likely to be produced as described earlier.

For patients with anorexia and/or the like, certain embodiments of the invention decrease secretion of gonadotropin-releasing hormone (GnRH), luteinizing hormone releasing hormone (LHRH), and/or thyrotropin releasing hormone (TRH) by the arcuate nucleus 106. Such inhibitory stimulation is likely to be produced as described earlier.

In some embodiments of the invention, for patients with obesity and/or the like, the stimulation inhibits the effects of gamma-aminobutyric acid (GABA) on the ventromedial nucleus 104 of the hypothalamus and/or any other neural tissue with receptors for GABA. Such inhibitory action is likely to be produced by high-frequency electrical stimulation, an antagonist(s) of GABA (e.g., bicuculline), and/or the like.

For patients with anorexia and/or the like, certain embodiments of the invention produce or enhance the effects of gamma-aminobutyric acid (GABA) on the ventromedial nucleus 104 of the hypothalamus and/or any other neural tissue with receptors for GABA. Such excitatory action is likely to be produced by low-frequency electrical stimulation, a GABA agonist(s) (e.g., baclofen and/or muscimol), GABA itself, and/or the like.

In various embodiments, sensing means described earlier may be used to orchestrate first the activation of SCU(s) targeting an area(s) of the brain, and then, when appropriate, the SCU(s) targeting another area(s) and/or by a different means. Alternatively, this orchestration may be programmed, and not based on a sensed condition.

Additional potential (but not necessary) uses of the present invention include, but are not limited to, treatment for and prevention of diabetes and other conditions caused or worsened by obesity and/or other eating disorders, via the promotion of normal metabolism and weight control.

In one embodiment of the invention, differential placement and/or activation of electrodes produces orexigenic, appetite increasing, or anorexigenic, appetite decreasing effects. Thus, in one embodiment of the invention, methods and systems are provided for treating food addiction or aversion through electrical stimulations of regions of the brain associated with craving and satiation.

The pathological eating disorders Anorexia Nervosa (AN) and Bulimia Nervosa (BN) are associated with profound structural and functional changes in the brain. Anorexia nervosa (AN) involves hypothalamo-pituitary dysfunction including failed hypertrophy of the pituitary in puberty. Structural studies of the brain performed by imaging with computed tomography (CT) and magnetic resonance imaging (MRI) revealed that atrophy of brain structures in chronic and severe AN, including loss of grey matter, is not restored even after weight restoration. Functional studies of the brain performed with positron emission tomography (PET), single photon emission CT (SPECT) and functional MRI (fMRI) in AN patients has revealed that the prefrontal cortex is critical for processing of food-related information and that hypoactivity in this region before eating may correspond to hypophagia and general disinterest in food. Higher activity in this region after eating may be associated with anxiety occurring after food intake or with food related anxiety in anticipation of eating. (Stamatakis and Heterington, *Nutritional Neuroscience* 6 (2003) 325).

Brain imaging for abnormalities of critical neurotranismitters has shown abnormalities in 5-HT (serotonin) receptor binding that may be fundamental to AN. Similarly, investigations in bulimia nervosa (BN) have shown reduced thalamic and hypothalamic serotonin receptor transporter availability in BN that increases with disease duration. BN affects individuals across the weight spectrum from below normal weight to obesity. As with AN, BN is associated with pronounced differences in frontal and prefrontal regions. In obese binge eating women, regional cerebral blood flow (rCBF) was found to be increased in the left hemisphere when exposed to food as compared with non-binge eating controls). (Stamatakis and Heterington, *Nutritional Neuroscience* 6 (2003) 325). Because of the profound and irreversible changes in brain structure in severe or long duration AN or BN, early treatment is of particular value. The present invention permits specific tuned stimulation not only to particular brain structures but also permits isolated hemispheric stimulation to normalize hemispheric rCBF in response to food challenges. Regional normalization of this type is a particular advantage of the present invention that cannot be achieved with systemically administered medications even if such were available.

Thus, in one embodiment of the invention, the patient can manually activate the device to provide local stimulation that controls aversion or craving sensations. Alternatively, an SCU dedicated to sensory processes such as detection of rCBF communicates with an SCU that provides the stimulation pulses and/or drug infusion. In some embodiments, the parameters used by SCU 160 are automatically adjusted based on the sensed information. Thus, the electrical and/or drug stimulation parameters are adjusted in a closed-loop manner to provide stimulation tailored to the need for and/or response to the electrical and/or drug stimulation.

In one embodiment of the invention implantable microstimulator SCU 160 is sufficiently small to permit placement in or adjacent to the structures to be stimulated. For instance, in these configurations, capsule 152 may have a diameter of about 4-5 mm, or only about 3 mm, or even less than about 3 mm. In these configurations, capsule length may be about 25-35 mm, or only about 20-25 mm, or even less than about 20 mm. Particularly small microstimulators may be particularly desirable in certain patients where pathologic concern over appearance may be a paramount consideration in the patients acceptance of the therapy.

In other embodiments, the SCU is not limited to a miniature form factor. For example, where the electrodes and/or drug infusion catheter outlets are relatively remote from the SCU, the SCU may be a microstimulator or may alternatively be a larger SCU. The remote SCU can be implanted, such as for example percutaneously and connected to the electrodes and/or drug delivery catheters that are also implanted percutaneously. The power source of the SCU is realized using one or more of the following options, or the like: (1) an external power source coupled to the SCU via a radio-frequency (RF) link; (2) a self-contained power source for generation or storage of energy, e.g., a primary battery, a replenishable or rechargeable battery, a capacitor, a supercapacitor; and/or (3) if the self-contained power source is replenishable or rechargeable, replenishing or recharging the power source can be provided by an RF link, an optical link, or other energy-coupling link. The electrodes can be single or multiple and specifically placed. According to some embodiments of the invention, the electrodes used for electrical stimulation are arranged as an array on a thin implantable lead.

Alternatively, where a large area of the brain such as the prefrontal cortex requires differential stimulus, the electrodes can be formed in a two dimensional array or grid that is placed under the skull bones but over the dura of the brain as depicted in FIG. 8. Various of the plurality of individual electrodes 290 in the array 292 can be differentially activated and deactivated according to a variety of stimulation parameters to achieve optimal therapy for the patient. In one embodiment of the invention, the array is embedded in a mesh, such as for example mesh 295. A plurality of leads 170*n* may be bundled and connect the array 292 to SCU 160. In one embodiment of the invention, the two dimensional array is first utilized to specifically map areas that are active in the particular patient during hunger, craving and/or satiation. After the mapping, the two dimensional array is removed and replaced with individual leads and/or linear electrode arrays.

The SCU may include circuitry for stimulating a nerve or infusing a stimulating drug(s) either intermittently or continuously. Specific stimulation/infusion parameters may provide therapy for, e.g., varying types and degrees of severity of addiction or eating disorders.

The SCU used with the present invention possesses one or more of the following properties, among other properties: at least one electrode for applying stimulating current to surrounding tissue and/or a pump and at least one outlet for delivering a drug or drugs to surrounding tissue; electronic and/or mechanical components encapsulated in a hermetic package made from biocompatible material(s); electrical circuitry inside the package that receives and/or stores power and/or receives or transmits data by inductive or radio-frequency (RF) coupling to transmitting circuitry placed outside the body, thereby avoiding need for electrical leads to connect devices to a central implanted or external controller. In some embodiments the SCU is characterized by a form factor that permits the SCU to be implantable in a depression or opening in the skull, or within the brain.

Food craving (defined as an intense desire to eat a specific food) is of interest because it is extremely common and influences obesity and nutritional status. Food craving may be ameliorated by stimulating areas of the brain associated with hunger and satiation. In one embodiment, areas for placement of electrodes and/or drug delivery catheter outputs include the ventromedial nucleus of the hypothalamus (VMH), which is strongly implicated in regulation of food intake. FIG. 1B illustrates the relative location of the VMH 104 in relation to the paraventricular nucleus of the hypothalamus (PVN) 100. Destructive lesions in the VMH are known to lead to hyperphagia, reduced energy expenditure, and obesity. Because a lesion to the VMH causes an animal to eat voraciously; this area has thus been hypothesized to be "the satiety center." In addition, for centrally administered NPY, the VMH is believed to be a crucial site of NPY-induced feeding. The PVN receives significant input from the NPY-secreting neurons of the arcuate nucleus 106 and is an important region for regulation of hunger. Increased secretion of NPY leads to abnormally increased appetite for food (hyperphagia), increased body weight, and reduced energy expenditure. Destructive lesions in the PVN lead to hyperphagia, reduced energy expenditure, and obesity in otherwise normal subjects. In one embodiment of the present invention, the effect of destruction or a lesion in the VMH and/or the PVN is mimicked by stimulation at a high frequency (greater than about 100 Hz) to treat anorexia nervosa. Conversely, in another embodiment of the invention, the VMH and/or the PVN is stimulated at low activating frequencies (less than about 100 Hz) to inhibit hunger in the treatment of obesity. In one embodiment of the invention, electrodes are placed in at least both of the VMH 104 and the PVN 100 to permit fine control over hunger and satiation and to prevent accommodation.

In another embodiment of the invention, electrodes are placed for stimulation of the arcuate nucleus 106 of the hypothalamus to modulate release of NPY. Inhibitory electrical stimulation at a high frequency (greater than about 100 Hz) is used to inhibit release of NPY to treat obesity. Conversely, in another embodiment of the invention, the low activating frequencies (less than about 100 Hz) are used to stimulate the arcuate nucleus to release NPY in the treatment of anorexia. Referring to FIG. 1B for the relative location of the arcuate nucleus 106, the VMH 104 and the PVN 100, in one embodiment of the invention, electrodes are placed for stimulation of the arcuate nucleus 106 in addition to either or both of the VMH 104 and the PVN 100 to permit fine control over hunger and satiation and to prevent-accommodation.

Although the hypothalamus has been strongly implicated in regulation of appetite, other areas of the brain are also important in this regard. FIGS. 9A and B depict several of the structures of the brain that are important to the regulation of hunger and satiation. PET scan and MRI studies show that when hungry, neuronal activity increases not only in the hypothalamus 300, but also in the thalamus 305, anterior region of the cingulate cortex 310, amygdala 315, caudate 320, orbitofrontal cortex (OFC) 322, insula cortex 324, hippocampal 326 and parahippocampal formations 328, medulla 340, and striatum (not shown). When full, neuronal activity increases in the ventromedial and dorsolateral areas of the prefrontal cortex 345, interior parietal lobe 325, lateral orbitofrontal cortex (not shown) and temporal cortex 380. Thus, in one embodiment of the invention, electrodes and/or drug delivery catheter outflows are positioned in one or more these locations for control of craving and satiation.

Interpretation of PET scan studies have further indicated that the hypothalamus 300, thalamus 305, insula 324, hippocampal 326/parahippocampal formation 328, orbitofrontal cortex 322 and basal ganglia represent a primary hunger stimulation (orexigenic) network. Upon satiation, the prefrontal cortex suppresses this response via inhibitory projections into this network, and in particular the lateral hypothalamus. (Del Parigi A. et al. *Annals of the New York Academy of Sciences* 967 (2002)389-397). The present invention provides modalities able to intervene and control this network.

In one embodiment the prefrontal cortex is activated via low frequency (less than about 100 Hz) electrical stimulation to provide indirect inhibition of the hypothalamus, basal ganglia, temporal cortex, cerebellum, insular cortex, anterior cingulate, and orbitofrontal cortex for the treatment of obesity. Alternatively, inhibitory high frequency electrical stimulation (greater than about 100 Hz) is applied to directly to one or more of the hypothalamus, basal ganglia, temporal cortex, cerebellum, insular cortex, anterior cingulate, and/or orbitofrontal cortex for inhibition of hunger in the treatment of obesity.

Conversely, in another embodiment of the invention, the prefrontal cortex is stimulated at high inhibitory frequencies (greater than about 100 Hz) to inhibit the prefrontal cortex from releasing hunger inhibitory stimuli in the treatment of anorexia and other food aversion disorders including depressed appetite in certain wasting disorders and depressed appetite in conjunction with cancer therapies. Alternatively, stimulatory low frequency electrical stimulation (less than about 100 Hz) is applied to directly to one or more of the hypothalamus, basal ganglia, temporal cortex, cerebellum, insular cortex, anterior cingulate, and/or orbitofrontal cortex for stimulation of hunger in the treatment of anorexia and other food aversion disorders including depressed appetite.

Stimulation of the hippocampus, insula, and caudate: Recent studies provide neuroanatomical linkages between food cravings and cravings for drugs and alcohol. Functional magnetic resonance imaging (fMRI) studies examining food craving have shown craving-related changes in fMRI signals in the hippocampus 326, insula 324, and caudate nucleus 320, three areas reported to be involved in drug craving. The insula 324 (island of Reil) lies deeply in the lateral or Sylvian fissure, and is surrounded by a deep circular sulcus which separates it from the frontal, parietal, and temporal lobes. The caudate nucleus 320 (nucleus caudatus; caudatum) is a pear-shaped gray mass having its broad area or head directed forward into the anterior cornu of the lateral ventricle and its narrow end, or tail, directed backward on the lateral side of the thalamus. In one embodiment of the invention, electrodes are positioned in one or more the hippocampus 326, parahippocampus 328, the insula cortex 324, especially the anterior insula, and caudate 320. Further areas for electrode and/or drug delivery catheter placement include the putamen 330, especially the dorsal putamen. After or during placement, the response of the individual patient can be tuned and then controlled by customized programming. Electrodes and/or drug delivery catheters are placed in one or more of these sites for control of craving and satiety.

Stimulation of the VTA and NAc: FIG. 10 illustrates a lateral cross section of the brain showing the position of the ventral tegmental area (VTA) 370 relative to the nucleus accumbens (NAc) 375, arcuate nucleus of the hypothalamus 106, paraventricular nucleus of the hypothalamus (PVN) 100, pituitary 390, amygdala 315, cingulate cortex (CING) 310, and hippocampus 326.

A principal area of the brain associated with addiction is the ventral tegmentum or the ventral tegmental area (VTA) of the midbrain, an area that lies close to the substantia nigra and the red nucleus. The VTA is considered to be part of the pleasure or reward system, which influences incentive and motivation as well as addiction. This area is rich in dopamine and serotonin neurons and is part of two major dopamine pathways: the mesolimbic pathway, which connects the VTA to the nucleus accumbens (NAc), and the mesocortical pathway, which connects the VTA to cortical areas in the frontal lobes. The NAc terminals originating in the VTA are the site of action of highly addictive drugs such as cocaine and amphetamine which cause a several-fold increase in dopamine levels in the NAc. In addition to cocaine and amphetamine, almost every drug abused by humans has been shown to increase dopamine levels in the NAc. Severing projections between the VTA and the NAc terminates dopamine transfer and results in cessation of addiction. Dopamine release via this pathway is thus a shared characteristic of all addictions.

The NAc (lateral or medial) is a collection of neurons in the basal forebrain region is part of the ventral continuation of the dorsal striatum and shares general principles of connectivity with the striatum. The NAc is also called ventral striatum. The principle neuronal cell type of the NAc is the medium spiny neuron which produces gamma amino butyric acid (GABA) and are the main projection or output neurons of the NAc. GABA is the main inhibitory central nervous system (CNS) neurotransmitter. Other neuronal types found in the NAc include large aspiny cholinergic interneurons.

The output neurons of the NAc project via axons into the ventral portion of the globus pallidus known as the ventral pallidum (VP), which, in turn, project to the mediodorsal (MD) nucleus of the thalamus, which projects to the prefrontal cortex. Considering that the major input neurons to the NAc include the prefrontal cortex and dopaminergic neurons located in the ventral tegmental area (VTA) which connect via the mesolimbic pathway, the NAc participates in a cortico-striato-thalamo-cortical loop.

In one embodiment of the invention, electrodes and/or drug delivery catheters are positioned in the VTA for control of additive cravings. In another embodiment, electrodes and/or drug delivery catheters are positioned in the NAc for control of addictive cravings. In one embodiment, the NA is stimulated for activation in eating disorders but is stimulated to inhibit for obesity. Thus low-frequency electrical stimulation (i.e., less than about 100 Hz) is used to increase activity in the NAc for treatment of anorexia. High-frequency electrical stimulation (i.e., greater than about 100 Hz) is used to inhibit activity in the NAc for treatment of obesity. In a further embodiment, several electrodes and/or drug delivery catheters are positioned, including in the VTA and/or the NAc as well as one or more the hippocampus, insula, and caudate such that the response of the individual patient can be tuned and then controlled by customized programming.

Serotonin, as well as the other monoamine neurotransmitter noradrenaline, are the target for several of the anorectic (appetite lowering) agents that are marketed for the treatment of obesity such as the β-phenethylamine derivatives (sibutramine or Meridia) that selectively inhibit the reuptake (destruction) of both noraepinephrine and serotonin (5-hydroxytryptamine or 5-HT) and, to a lesser extent, dopamine. Thus, in one embodiment of the invention, electrodes are placed in the VTA and/or the NAc for treatment of obesity.

Stimulation of Limbic System Structures: The amygdala is located in the medial temporal lobe and forms part of the limbic system. The amygdala is believed to play a key role in emotions and is linked to both fear responses and pleasure. The amygdala is a complex of several separately functioning nuclei grouped together by anatomical proximity. Primary constituents of the amygdala are the basolateral complex (BLA), the central or centromedial nucleus and the cortical nucleus. The basolateral complex receives input from sensory systems and is necessary for fear conditioning. The centromedial nucleus is the main output for the basolateral complex and is involved in emotional arousal. The centromedial nucleus sends outputs to the hypothalamus for activation of the sympathetic nervous system, the reticular nucleus for increased reflexes, the trigeminal nerve and facial nerve for facial expressions of fear, and the ventral tegmental area, locus ceruleus, and laterodorsal tegmental nucleus for activation of dopamine, norepinephrine and epinephrine. The cortical nucleus is involved in olfaction and pheromone processing. In one embodiment of the invention, low frequency stimulation (i.e., less than 50-100 Hz) is applied to the amygdala to activate it without shutting it down.

Stimulation of Forebrain Cerebral Areas: In studies involving presentation of appetitive food stimuli and analysis using PET and FDG, it was found that food presentation significantly increased metabolism in the whole brain (24%, P<0.01) and these changes were largest in superior temporal, anterior insula, and orbitofrontal cortices. In particular, increases in the right orbitofrontal cortex were correlated significantly with the increases in self-reports of hunger and desire for food. Wang G J et al. *Neuroimage*. 2004 April; 21(4):1790-7. Thus, the ventromedial prefrontal cortex, dorsolateral prefrontal cortex, interior parietal lobe, right orbitofrontal cortex and temporal cortex are targets for electrical and/or drug stimulation for appetite modulation. In one embodiment the prefrontal cortex is activated via low frequency (less than about 100 Hz) electrical stimulation to provide indirect inhibition of the hypothalamus, basal ganglia, temporal cortex, cerebellum, insular cortex, anterior cingulate, and orbitofrontal cortex for the treatment of obesity. Conversely, in another embodiment of the invention, the prefrontal cortex is stimulated at high inhibitory frequencies (greater than about 100 Hz) to inhibit the prefrontal cortex from releasing hunger inhibitory stimuli in the treatment of anorexia and other food aversion disorders including depressed appetite in certain wasting disorders and depressed appetite in conjunction with cancer therapies.

Stimulation at Multiple Sites to Prevent Accommodation: In some individuals and conditions, accommodation, or resistance to stimulation, either subacutely or progressively, may occur if only one center of the brain is stimulated. Thus, in one embodiment of the invention, electrodes are placed in several locations including central craving or satiety controller, including the arcuate nucleus, PVN, and amygdala. In one embodiment of the invention, electrodes are placed in at least both of the VMH 104 and the PVN 100 to permit fine control over hunger and satiation and to prevent accommodation. In one embodiment of the invention, for patients suffering from anorexia or the like, inhibitory stimulation including high frequency electrical stimulation is applied to the nucleus of the solitary tract 110 in addition to the VMH 104 and the PVN 100.

In another embodiment of the invention, electrodes are placed in two or more of the following sites: hypothalamus, amygdala, insula cortex, medulla, striatum, caudate, thalamus, orbitofrontal cortex, anterior cingulate cortex, hippocampal and parahippocampal formations, ventromedial prefrontal cortex, dorsolateral prefrontal cortex, interior parietal lobe, lateral orbitofrontal cortex, nucleus of the solitary tract and temporal cortex. Thus, in one embodiment of the invention, electrodes and/or drug delivery catheter outflows are positioned in one or more these locations for control of craving and satiation.

In one embodiment of the invention, electrodes are placed in several locations including the solitary tract nucleus 110, the VTA 300, the amygdala 312, particularly the basolateral amygdala (BLA), the anterior of the cingulate cortex 314, the hypothalamus, including the arcuate nucleus of the hypothalamus (ARC) 106, lateral nucleus of the hypothalamus (LHA), paraventricular nucleus of the hypothalamus (PVN) 100, and the ventromedial hypothalamic nucleus (VMH) 104.

Further areas for electrode placement include the putamen, especially the dorsal putamen, the hippocampus and parahippocampus, the insula cortex, especially the anterior insula, the nucleus accumbens (NAc), the medulla, caudate, thalamus, ventral striatum, and in one or more cerebral locations in the forebrain including the dorsolateral and/or ventromedial prefrontal cortex, temporal cortex, lateral orbitofrontal cortex and inferior parietal lobule.

In one embodiment of the invention, electrodes are placed in areas that are important for stimulation of hunger as well as those responsible for satiety. Depending on whether the individual is suffering from an orexic or an anorexic condition, the differently placed electrodes are tuned to high or low frequency emission to stimulate or suppress responses. Thus, electrodes are placed in several areas of the brain active during hunger selected from the hypothalamus, amygdala, insula cortex, medulla, striatum, caudate, thalamus, orbitofrontal cortex, anterior cingulate cortex, hippocampus and parahippocampus. Electrodes are further placed in several areas of the brain active when satiated selected from the ventromedial prefrontal cortex, dorsolateral prefrontal cortex, interior parietal lobe, lateral orbitofrontal cortex and temporal cortex.

Control of Fat Intake: Of the appetite stimulating mediators, norepinephrine and neuropeptide Y, appear to predominantly stimulate carbohydrate intake. In one embodiment of the invention, selective inhibition of carbohydrate intake is effected while sparing the desire for protein intake. In PET studies of rCBF in AN patients and controls, higher subjective reports of desire to eat was found with high versus low calorie food stimulus. (Stamatakis and Heterington, *Nutritional Neuroscience* 6 (2003) 325). Differential blood flow changes in the temporo-insular cortical and medial temporal lobes were noted in response to high calorie conditions. However, in controls as compared with the AN patients, the changes in medial temporal lobe blood flow were bilateral. Furthermore, AN patients exhibited exaggerated responses in the visual association cortex in response to high calorie food, possibly associated with the phobic aversion to fat.

A further functional study of the areas of the brain associated with glucose ingestion found activation in the supplementary motor area, somatosensory cortex, cerebellum, anterior cingulated and orbitofrontal cortex (OFC), while negative activation was recorded in the hypothalamus, which is an area of the brain associated with regulating plasma glucose concentration of control of food intake. Thus, in one embodiment of the invention, electrode placement and differential tuned stimulation are applied to reduce the desire for intake of fatty and high carbohydrate foods while sparing the desire for consumption of low calorie, low carbohydrate foods.

Control of Basal Metabolic Rate: Control of body weight is not limited to food intake, but also to metabolic demands. The basal metabolic rate can be stimulated to increase through activity of several organs including the hypothalamus, thyroid, pituitary and locus coeruleus (which releases norepinephrine). The hypothalamus contributes to the basal metabolic rate via several pathways. The anterior portion of the hypothalamus includes the suprachiasmatic nucleus (SCN) which project to other hypothalamic nuclei and sets circadian rhythms such as in sleep, hormone secretion, feeding and drinking. The organum vasculosum lamina terminalis (OVLT), just anterior to the SCN, is adjacent to unusually permeable capillaries that allow the OVLT to monitor blood constituents. Neurons near the OVLT are sensitive to changes in blood constituents such as sodium, water, and hormones such as angiotensin and atrial natriuretic hormone. Other circumventricular organs near the hypothalamus include the median eminence, just below the hypothalamus. Insulin diffuses from permeable capillaries in the median eminence to influence the hypothalamic regulation of feeding.

The middle portion of the hypothalamus includes the paraventricular nucleus (PVN) 100. Neurons from the PVN that project to the posterior pituitary contain vasopressin (antidiuretic hormone) and oxytocin. Smaller PVN neurons project to other portions of the brain including the preganglionic neurons in the intermediolateral horn (T1-L2) of the spinal cord which control the sympathetic nervous system, preganglionic neurons in the dorsal motor nucleus of the Vagus (DMN of Xth nerve), which regulate the parasympathetic control of gastrointestinal motility and insulin secretion, and neurons in the Nucleus of Tractus Solitarius and Hypoglossal Nucleus which regulate swallowing and tongue movement.

In one embodiment of the invention, the basal metabolism is raised by electric stimulation of the paraventricular nucleus of the hypothalamus (PVN) to release somatostatin and/or the dorsomedial nucleus of the hypothalamus to release thyrotropin releasing hormone (TRH). Both somatostatin and TRH then act on the pituitary to release thyroid stimulating hormone (TSH) which is a primary regulatory of metabolic rate through release of T3 and T4. Alternatively or in addition, the supraoptic nucleus of the hypothalamus is electrically stimulated to release growth-hormone releasing hormone (GHRH) which in turn stimulates the pituitary to release growth hormone (GH), which is an important stimulant for growth of muscle.

In one embodiment of the invention, the pituitary is stimulated electrically in lieu of, or in addition to the hypothalamus for the regulation of metabolic rate. The pituitary gland, or hypophysis, in the small, bony cavity (sella turcica) at the base of the brain. The posterior pituitary lobe (neurohypophysis) can be considered a projection of the hypothalamus connected to the hypothalamus by the tuberoinfundibular pathway. The neurohypophysis does not produce its own hormones, but stores and releases oxytocin and antidiuretic hormone (ADH). The anterior pituitary lobe (adenohypophysis) receives releasing hormones from the hypothalamus by a portal vein system. The anterior pituitary secretes growth hormone, prolactin, follicle-stimulating hormone, luteinizing hormone, thyroid-stimulating hormone, adrenocorticotropic hormone, endorphins and other hormones. The anterior and posterior pituitary are separated in humans by a thin layer of cells termed the intermediate lobe in many animals. The intermediate lobe produces melanocyte-stimulating hormone (MSH). Elevation of basal metabolism through electrical stimulation can be used alone or in conjunction with appetite modification as described herein.

While the invention herein disclosed has been described by means of specific embodiments and applications thereof, numerous modifications and variations could be made thereto by those skilled in the art without departing from the scope of the invention set forth in the claims.

What is claimed is:

1. A method of treating a patient with an alcohol addiction, comprising:
    implanting one or more system control units in the patient, wherein one or more of the system control units are connected to and control one or more electrodes and/or drug delivery catheters that are implanted in the brain of the patient; and
    delivering a stimulus configured to treat the alcohol addiction with one or more of the system control units via the one or more electrodes and/or drug delivery catheters to at least one of an anterior insula and a dorsal putamen.

2. The method of claim 1, wherein the one or more system control units are configured to receive power and/or data by RF transmission.

3. The method of claim 1, wherein the one or more system control units are percutaneous and connected to one or more electrodes by a percutaneous lead.

4. The method of claim 1, wherein the one or more system control units are configured to receive power and/or data by direct electrical connection.

5. The method of claim 1, wherein the one or more system control units comprises at least one microstimulator.

6. The method of claim 1, wherein the stimulus is configured to prevent accommodation.

7. The method of claim 1, further comprising customizing the stimulus to the patient.

8. The method of claim 1, wherein the stimulus comprises electrical stimulation delivered via the one or more electrodes.

9. The method of claim 1, wherein the stimulus comprises one or more drugs delivered via the drug delivery catheters.

10. The method of claim 1, further comprising sensing at least one condition related to the alcohol addiction and adjusting the stimulus according to the sensed condition.

11. A method of treating a patient with an eating disorder, comprising:
    electronically sensing at least one condition indicating a need for stimulus to one or more brain areas in the patient that are related to said eating disorder by a sensor that sends an electronic signal to at least one system control unit, thereby activating the at least one system control unit; and
    delivering a stimulus via one or more electrodes and/or drug delivery catheters that are implanted in the brain of the patient and that are controlled by the activated at least one system control unit, wherein the stimulus is delivered to the one or more areas of the brain related to said eating disorder;
    wherein the one or more areas of the brain related to said eating disorder comprise at least one or more of a nucleus of the solitary tract, an insula cortex, a medulla, and a parahippocampus.

12. The method of claim 11, wherein the sensed condition comprises at least one of a regional cerebral blood flow (rCBF), an impedance, a pH level, an electrical activity of the brain, a nerve activity, a muscle activity, a neurotransmitter level, a neurotransmitter breakdown product level, a hormone level, a ketone level, a glucose level, an electrolyte level, an enzyme level, a cytokine level, a medication level, a drug level, and a level of a bloodborne substance.

13. The method of claim 11, wherein the stimulus comprises a compound that increases excitement of at least one area of the brain that exhibits chronic decreased activity.

14. The method of claim 11, wherein the stimulus comprises at least one or more of an excitatory neurotransmitter agonist, a medication that increases levels of at least one excitatory neurotransmitter, an excitatory hormone agonist, an inhibitory neurotransmitter antagonist, an inhibitory hormone antagonist, corticotropin releasing factor, a corticotropin releasing factor agonist, bombesin, a bombesin agonist, glucagon-like peptide 1, a glucagon-like peptide 1 agonist, serotonin, a serotonin agonist, leptin, a leptin agonist, a ghrelin antagonist, an AGRP antagonist, an MC4-R agonist, an MC3-R agonist, an orexin-A antagonist, an orexin-B antagonist, an OX1R antagonist, an OX2R antagonist, cholecystokinin, a cholecystokinin agonist, dopamine, dynorphin, melanin-concentrating hormone, melanocyte-stimulating hormone, growth hormone-releasing hormone (GHRH), endocannobinoids, beta-endorphin, and galanin.

15. The method of claim 11, wherein the stimulus comprises a compound that decreases excitement of at least one area of the brain that exhibits chronic increased activity.

* * * * *